US006274147B1

(12) United States Patent
Vakharia et al.

(10) Patent No.: US 6,274,147 B1
(45) Date of Patent: Aug. 14, 2001

(54) METHOD FOR GENERATING NONPATHOGENIC INFECTIOUS PANCREATIC NECROSIS VIRUS (IPNV) FROM SYNTHETIC RNA TRANSCRIPTS

(75) Inventors: Vikram N. Vakharia, Bowie; Kun Yao, College Park, both of MD (US)

(73) Assignee: University of Maryland-Biotechnology Institute, College Park, MD (US)

( * ) Notice: Subject to any disclaimer, the term of this patent is extended or adjusted under 35 U.S.C. 154(b) by 0 days.

(21) Appl. No.: 09/282,147

(22) Filed: Mar. 31, 1999

Related U.S. Application Data
(60) Provisional application No. 60/080,178, filed on Mar. 31, 1998.

(51) Int. Cl.[7] .............................. A61K 39/12; C12N 7/01; C12N 7/04; C12N 15/40; C12N 15/86
(52) U.S. Cl. ..................... 424/199.1; 424/204.1; 424/205.1; 435/235.1; 435/236; 435/320.1; 435/325; 435/472; 536/23.72
(58) Field of Search ................... 435/235.1, 236, 435/325, 320.1, 472; 536/23.72; 424/205.1, 204.1, 199.1

(56) References Cited

U.S. PATENT DOCUMENTS
5,871,744 * 1/1999 Vakharia et al. .................. 424/205.1

FOREIGN PATENT DOCUMENTS
| 887412 | * 12/1998 | (EP) | ............................. C12N/15/40 |
| WO 95/26196 | 10/1995 | (WO) | ............................. A61K/35/76 |
| WO 98/09646 | 3/1998 | (WO) | ............................. A61K/39/00 |
| WO 99/16866 | 4/1999 | (WO) | ............................. C12N/7/04 |

OTHER PUBLICATIONS

Pettersen. "Infectious pancreatic necrosis virus (IPNV) and the development of a viral vaccine." Norsk Veterinaer 109 (8–9):p499–505 (Abstract only cited), 1997.*

Lee et al. Applied & Environmental microbiology 62(7):2513–2520, 1996.*

Mundt et al., "Synthetic Transcripts of Double–stranded Birnavirus Genome are Infectious", Oct. 1996, pp. 11131–11136, vol. 93, Proc. Natl. Acad. Sci, USA.

Mundt et al., "VP5 Infectious Bursal Disease Virus in not Essential for Viral Replication in Cell Culture", Jul. 1997, pp. 5647–5651, vol. 71, No. 7, Journal of Virology.

Heppell et al., "Characterization of the Small Open Reading Frame on Genome Segment A of Infectious Pancreatic Necrosis Virus", 1995, pp 2091–2096, vol. 76, Journal of General Virology.

Yao et al. "Generation of Infectious Pancreatic Necrosis Virus from Cloned cDNA", Nov. 1998, pp. 8913–8920, vol. 72, No. 11, Journal of Virology.

Yao et al., "Generation of a Mutant Infectious Bursal Disease Virus That Does Not Cause Bursal Lesions", Apr. 1998, pp. 2647–2654, vol. 72, No. 4, Journal of Virology.

* cited by examiner

Primary Examiner—Mary E. Mosher
(74) Attorney, Agent, or Firm—Arent Fox Plotkin Kintner Kahn PLLC.

(57) ABSTRACT

A system for the generation of live, nonpathogenic infectious pancreatic necrosis virus (IPNV), a segmented double-stranded (ds)RNA virus of the Birnavirdae family, using synthetic transcripts derived from cloned DNA has been developed. Independent full-length cDNA clones were constructed which contained the coding and non-coding regions of RNA segments A and B of IPNV, respectively. Segment A was modified to prevent the expression of NS protein. Synthetic RNAs of both segments were produced by in vitro transcription of linearized plasmids with T7 RNA polymerase. Transfection of CHSE cells with combined plus-sense transcripts of both segments generated infectious virus. The development of a system for producing NS protein deficient IPNV will greatly facilitate studies of viral pathogenesis, and the development of live attenuated vaccines for IPNV.

24 Claims, 12 Drawing Sheets

(5 of 12 Drawing Sheet(s) Filed in Color)

The 5' and 3'- non-coding Regions of IPNV Segment A

```
          nt 1                                                              62
JAS-5'NC     GGAAAGAGAGAGTTTCAACGTAGTGTAGTGGTAACCCACGAGCGGAGAGCTCTTACGGAGGAGCTCTC
WB-5'NC      GGAAAGAGAGT----------------------------------------------------
SP-5'NC      GGAAAGAGAGT-----------------------------C----------------------

(NSP)
JAS-5'NC     CGTCGATGGCGAAAGCCCTTCTAACAAACAACCAACAATTCTTATCTACATGAATCATG (122)
WB-5'NC      -A-----------------------------------A---AC-A-----------ATG (121)
SP-5'NC      ---------------------------------------A---AC-A------A-CA---C-AGATG (121)

nt 3036                                                         3097
JAS-3'NC     TAACAGCTACTCTCTCTTTCCTGACTGATCCCCTGGCCGTAACCCCGGCCCCCCCAGGGGCCCC
WB-3'NC      TAA----ACTCTCTTTCC---------------------T-------------------C
Sp-3'NC      TAA--A--ACTCTCTTTCC-----------------------AA---------------C
          nt 3035
```

The 5' and 3'-non-coding Regions of IPNV Segment B

```
          nt 1                                                                            62
JAS-5'NC  GGAAACAGTGGGTCAACGTTGGTGGCACCCGACATACCACGACTGTTTACGTATGCACGCAA
WB-5'NC   ------------------------GTTGGTGGCAC-------------------------
Sp-5'NC   ------------------------GTTGGTGGCAC---------------------G---

JAS-5'NC  GTGCCCTTTAACAAAACCCTATAC ACACAACTCATGATA ATG      102
WB-5'NC   ------C-A-----T----- -- ---------------- ATG      102
Sp-5'NC   ----C---TTA----C-T---C-AT-T-----T------- ATG      103 nt 2636
JAS-3'NC  TAAGAAGACCCAA ACCGGGAAGAATCCGAAATGAATCAGCTGGACTCATATGAAAGCTCCG
WB-3'NC   TAA----GA---- -G---------------------------CC-----------AA---
Sp-3'NC   TAA-------- -G--G--AGGGAGCATCCGAAATGA----TG-A------C-A------

JAS-3'NC  CGCCGCACGGGCAAGCTGGACAAAAGTAGTGACCCGACAACGTGCCACCAACATGACCCCTG
WB-3'NC   ----T-A--------A-C---------------------------TGTGCCACCAAC----A-
Sp-3'NC   ---AG-A-----T-CAG--C---------------T--G-CAGTGCCACCAAC----A-

JAS-3'NC  AAAACATCCGGTTCCGCCAGGGACCCC   2784
WB-3'NC   -T-----C-- ----------------   2783
Sp-3'NC   -T-----   ------------------ 2777
```

METHOD FOR GENERATING NONPATHOGENIC INFECTIOUS PANCREATIC NECROSIS VIRUS (IPNV) FROM SYNTHETIC RNA TRANSCRIPTS

This application claims the benefit of U.S. Provisional Application No. 60/080,178, filed Mar. 31, 1998.

BACKGROUND OF THE INVENTION

Aquatic Birnaviruses such as infectious pancreatic necrosis virus (IPNV) are the causal agent of a highly contagious and destructive disease of juvenile Rainbow and Brook trout, and Atlantic salmon (Wolf, K. 1988, Fish viruses and fish viral diseases. Canstock Publishing Associates, Cornell University Press, Ithaca and London.). Highly virulent strains of IPNV can cause greater than 90% mortality in hatchery stocks less than four months old and survivors of infection can remain lifelong asymptomatic carriers, and serve as reservoirs of infection (McAllister, P. E., W. J. Owens, and T. M. Ruppenthal. 1987, Detection of infectious pancreatic necrosis virus in pelleted cell and particulate components from ovarian fluid of Brook trout (*Salvilimus fontindis*). Dis. Aquat. Org. 2:235–237). In survivors of an IPNV epizootic, the virus persists and can cause severe growth retardation in individual fish exhibiting virus persistence (McKnight and Roberts; Br. Ven. J. 132:76–86, 1976). In smolts, the virus produces considerable necrosis or inflammation of the pancreas. The virus is capable of infecting a number of different hosts and has a worldwide presence (Pilcher and Fryer. *Crit. Rev. Microbial.* 7:287–364, 1980).

IPNV belongs to a group of viruses called Birnaviridae which includes other bisegmented RNA viruses such as infectious bursal disease virus (chickens), tellina virus and oyster virus (bivalve mollusks) and drosophila X virus (fruit fly). These viruses all contain high molecular weight (MW) double-stranded RNA genomes. IPNV belongs to the Aquabirnavirus genus (Dobos, P. 1995, The molecular biology of infectious pancreatic necrosis virus (IPNV). Ann. Rev. Fish Dis. 5:24–54). Aquatic Birnaviruses infect marine and fresh water organisms such as fish, shrimp and other crustaceans, oysters and other mollusks.

IPNV in a brook trout hatchery was first reported in 1941(McGonigle *Trans. Am. Fish Soc.* 70,297, 1941). In 1960, the viral nature of the disease was confirmed (Wolf et al., *Proc. Soc. Exp. Biol. Med.* 104:105–110,1960). Since that time there have been isolations of the virus in a variety of fish species throughout the world, including various trout and salmon species, carp, perch, pike, eels and char, as well as mollusks and crustaceans. Acute disease has been reported primarily in a limited number of salmonid species, such as a trout and salmon.

Young fish (two-to four-month old) appear to be the most susceptible to IPNV infection, resulting in high mortality (Wolf et al. U.S. Dept. Int. Bur. Sport Fish and Wildlife, Fish Disease Leaflet 1:14, 1966; Frantsi and Savan. *J. Wildlife Dis.* 7:249–255, 1971). In trout, IPNV usually attacks young fry about five to six weeks after their first feeding. The affected fish are darker than usual, have slightly bulging eyes and often have swollen bellies. At the beginning of an outbreak, large numbers of slow, dark fry are seen up against water outflows, and fish are seen "shivering" near the surface. The shivering results from a characteristic symptom of the disease, a violent whirling form of swimming in which the fish rotate about their long axis. If the affected fish are examined, a characteristic white mucus is seen in the stomach. The pancreas appears to be the primary target organ for the virus, with the pancreatic fat cells or Islets of Langerhans being unaffected (McKnight and Roberts, *Br. Vot. J.* 132:76–86, 1976). The only organ besides the pancreas where viral lesions are consistently found is the intestine.

After an IPNV outbreak, the surviving fish generally become carriers of the virus. Trout that are carriers of the virus are a serious problem for the aqua-culture industry because the only control method currently available for eliminating the virus in carrier fish is destruction of these fish. Several factors, including age, species and water temperature, appear to influence the severity of infection and the subsequent establishment of the carrier state. Surviving carriers shed IPNV for the remainder of their lifetime (Billi and Wolf, *J. Fish. Res. Bd. Can.* 26:1459–1465, 1969; Yamamoto, *Can. J. Micro.* 21:1343–1347, 1975; Reno et al., *J. Fish. Res. Bd. Can.* 33:1451–1456, 1978). Therefore, IPNV is a pathogen of major economic importance to the aquaculture industry.

In view of the great deal of interest in developing a vaccine for IPNV a variety of approaches have been tried. One approach is the use of killed virus as vaccines. For example, if formalin-inactivated virus is injected intraperitoneally into four week post-hatch fry, the fish becomes immunized (Dorson, *J. Virol* 21:242–258, 1977). However, neither immersion of the fish into a liquid suspension of killed virus nor oral administration thereof was effective. Thus, the main problem with using killed virus is the lack of a practical method for administration of the vaccine as injection is impractical for large numbers of immature fish. Some investigators have suggested that the uptake of viral antigen by immersion might be improved if the virus was disrupted into smaller, sub-viral components, but viral disruption methods have resulted in loss of antigenicity (Hill and Way, "Serological Classification of Fish and Shellfish Birnaviruses," Abstract, First International Conference of the European Association of Pathology, Plymouth, England, 1983).

The use of attenuated viral strains has also been tried (Dorson, Abstract, International Conference on IPNV, Taloires, France, 1982). However, the earlier attenuated strains either fail to infect the fish or fail to induce protection. Strains with low virulence have been tested as vaccines for more virulent strains, but mortality from the vaccinating strain was either too high or protection was only moderate (Hill et al., "Studies of the Immunization of Trout Against IPN," in *Fish Diseases*, Third COPRAQ Session (W. Ahne, ed.), N.Y., pp. 29–36, 1980).

There are two distinct serogroups of IPNV, designated as serogroup A and B. Serogroup A contains 9 serotypes, whereas serogroup B contains a single serotype (Hill, B. J., and K. Way. 1995, Serological classification of infectious pancreatic necrosis (IPN) virus and other aquatic birnaviruses. Ann. Rev. Fish Dis. 5:55–77).

The IPNV genome consists of two segments of double-stranded RNA that are surrounded by a single-shelled icosahedral capsid of 60 nm diameter (Dobos, P. 1976. Size and structure of the genome of infectious pancreatic necrosis virus. Nucl. Acids Res. 3:1903–1919). The larger of the two genomic segments, segment A (3097 bp), encodes a 106-kDa polyprotein (NH2-pVP2-NS protease-VP3-COOH) which is cotranslationally cleaved by the viral protease to generate mature VP2 and VP3 capsid proteins (Dobos, P. 1977. Virus-specific protein synthesis in cells inflicted by infectious pancreatic necrosis virus. J. Virol. 21:242–258;

Duncan, R., E. Nagy, P. J. Krell, and P. Dobos. 1987, Synthesis of the infectious pancreatic necrosis virus polyprotein, detection of a virus-encoded protease, and fine structure mapping of genome segment A coding regions, J. Virol. 61:3655–3664). Segment A also encodes a 15–17 kDa arginine-rich nonstructural protein (NS) from a small open reading frame (ORF) which precedes and partially overlaps the major polyprotein ORF. Although this protein is not present in the virion, it is detected in IPNV-infected cells (Magyar, G., and P. Dobos. 1994 Evidence for the detection of the infectious pancreatic necrosis virus polyprotein and the 15–17 kDa polypeptide in infected cells and of the NS protease in purified virus. Virology 204:580–589). The genomic segment B (2784 bp) encodes VP1, a 94-kDa minor internal protein, which is the virion-associated RNA-dependent RNA polymerase (Dobos, P. 1995, Protein-primed RNA synthesis in vitro by the virion associated RNA polymerase of infectious pancreatic necrosis virus. Virology 208:19–25; Duncan, R., C. L. Mason, E. Nagy, J. A. Leong, and P. Dobos, 1991, Sequence analysis of infectious pancreatic necrosis virus genome segment B and its encoded VP1 protein: A putative RNA-dependent RNA polymerase lacking the Gly-Asp-Asp motif. Virology 181:541–552). In virions, VP1 is present as a free polypeptide, as well as a genome-linked protein, VPg (Calvert, J. G., E. Nagy, M. Soler, and P. Dobos. 1991, Characterization of the VPg-dsRNA linkage of infectious pancreatic necrosis virus. J. Gen. Virol. 72:2563–2567).

Although the nucleotide sequences for genome segments A and B of various IPNV strains have been published, the precise 5'- and 3'-noncoding sequences of these strains have not been determined or confirmed (Duncan, R., and P. Dobos. 1986, The nucleotide sequence of infectious pancreas necrosis virus (IPNV) dsRNA segment A reveals one large ORF encoding a precursor polyprotein. Nucl. Acids Res. 14:5934; Duncan, R., C. L. Mason, E. Nagy, J. A. Leong, and P. Dobos, 1991, Sequence analysis of infectious pancreatic necrosis virus genome segment B and its encoded VP1 protein: A putative RNA-dependent RNA polymerase lacking the Gly-Asp-Asp motif. Virology 181:541–552; Håvarstein, L. S., K. H. Kalland, K. E. Christie, and C. Endresen, 1990, Sequence of large double-stranded RNA segment of the N1 strain of infectious pancreatic necrosis virus: a comparison with other Birnaviridae. J. Gen. Virol. 71:299–3908). Unlike IBDV, there is extensive homology between the noncoding sequences of IPNV segments A and B. For example, 32 of 50 nucleotides at the 5'-noncoding region and 29 of 50 nucleotides at the 3'-noncoding region between the two segments are conserved. These termini should contain sequences that are important in packaging and replication of IPNV genome, as demonstrated for other double-stranded RNA viruses such as mammalian reoviruses and rotaviruses (Gorziglia, M. L. and P. L. Collins. 1992, Intracellular amplification and expression of a synthetic analog of rotavirus genomic RNA bearing a foreign marker gene: Mapping cis-acting nucleotides in the noncoding region. Proc. Nati. Acad. Sci. USA 89:5784–5788; Patton, J. T., M. Wentz, J. Xiaobo, and R. F. Ramig. 1996, cis-Acting signals that promote genome replication in rotavirus mRNA. J. Virol. 70:3961–3971; Wentz, M. J., J. T. Patton, and R. F. Ramig. 1996. The 3-terminal consensus sequence of rotavirus mRNA is the minimal promoter of negative-strand RNA synthesis. J. Virol. 70:7833–7841; Zou, S., and E. G. Brown. 1992. Identification of sequence elements containing signals for replication and encapsulation of the reovirus M1 genome segment. Virology 186:377–388).

In recent years, a number of animal RNA viruses have been recovered from cloned cDNA, such as polio virus (a plus-stranded RNA virus), influenza virus (a segmented negative-stranded RNA virus), and rabies virus (a nonsegmented negative-stranded RNA virus) (Enami, M., W. Luytjes, M. Krystal, and P. Palese. 1990. Introduction of site-specific mutations into the genome of influenza virus. Proc. Natl, Acad. Sci. USA 87:3802–3807; Racaniello, V. R., and D. Baltimore. 1981. Cloned poliovirus complementary DNA is infectious in mammalian cells. Science 214:916–919; Schnell M. J, T. Mebatsion, and K. K. Conzelmann. 1994, Infectious rabies viruses from cloned cDNA. EMBO J. 13:4195–4205). However, to date, there is no report of a recovered infectious dsRNA virus of aquatic species.

One of the present inventors recovered a virus of segmented dsRNA genome from synthetic RNAs only. The reverse genetics system for birnavirus was developed by one of the present inventors who demonstrated that synthetic transcripts of infectious bursal disease virus (IBDV) genome are infectious (Mundt, E., and V. N. Vakharia. 1996, Synthetic transcripts of double-stranded birnavirus genome are infectious. Proc. Natl. Acad. Sci. USA 93:11131–11136).

In order to develop a reverse genetics system for IPNV, full-length cDNA clones of segments A and B of the West Buxton and SP strains were constructed. Complete nucleotide sequences of these cDNA clones were determined, including the 5'- and 3'-noncoding regions. Furthermore, one of the cDNA clones was modified by site-directed mutagenesis to create a tagged sequence in segment B. Synthetic plus-sense RNA transcripts of segments A and B were produced by in vitro transcription reactions on linearized plasmids with T7 RNA polymerase, and used to transfect chinook salmon embryo (CHSE) cells. In this application, the recovery of IPNV from CHSE cells transfected with combined RNA transcripts of segments A and B is described.

In order to study the function of NS protein in viral pathogenesis, the present inventors constructed a cDNA clone of IPNV segment A, in which the initiation codon of the NS gene was mutated to prevent the expression of the NS protein. Using the reverse genetics system, a wild-type IPNV was generated, as well as a mutant IPNV that lacked the expression of the NS protein. The properties of the recovered wild-type IPNV and mutant IPNV in cell culture were compared and their pathological function in the host evaluated.

SUMMARY OF THE INVENTION

This invention relates to the infectious pancreatic necrosis virus (IPNV) that is associated with a highly contagious and destructive disease of juvenile Rainbow and Brook trout and Atlantic salmon. More particularly, this invention relates to the development of a reverse genetic system for infectious pancreatic necrosis virus (IPNV), a prototype virus of the Birnaviridae family, using plus-stranded RNA transcripts derived from cloned cDNA. Full-length cDNA clones of IPNV genome were constructed that contained the entire coding and noncoding regions of RNA segments A and B. Segment A encodes a 106 kDa precursor protein which is cleaved to yield mature VP2, NS protease, and VP3 proteins, whereas segment B encodes the RNA-dependent RNA polymerase, VP1. Plus-sense RNA transcripts of both segments were prepared by in vitro transcription of linearized plasmids with T7 RNA polymerase. Transfection of chinook salmon embryo (CHSE) cells with combined transcripts of segments A and B generated live IPNV after 10 days post-transfection. Furthermore, a transfectant virus containing a genetically tagged sequence was also generated to confirm the feasibility of this system. The presence and specificity of the recovered virus was ascertained by immunofluorescence staining of infected CHSE cells with rabbit anti-IPNV serum, and by nucleotide sequence analysis. Thus, the development of a reverse genetics system for IPNV will greatly facilitate studies of viral replication, pathogenesis, and design of a new generation of live attenuated vaccines.

As a first application of IPNV reverse genetics, and to study the function of NS protein in vivo, an NS-protein deficient virus has been generated and it has been demonstrated that the mutant virus can replicate, but will not induce lesions. It is believed that NS protein is directly involved in viral pathogenesis since the wild-type IPNV, expressing the NS protein, is able to elicit pathological response in the natural host. However, the mechanism by which the NS protein would exert its function remains to be seen.

The nonstructural proteins of animal viruses have been shown to play an important role in viral replication and pathogenesis. For example, in foot-and-mouth disease virus, a 16-kDa NS protein (leader protease) was shown to attenuate the virus in vitro and in vivo, but it was dispensable for viral replication (Brown, C. C., et al., 1996, J. Virol. 70:5638–5641; Piccone M. E., et al. 1995, J. Virol. 69:5376–5382). In chicken anemia virus (an immunosuppressive virus), a basic, cysteine and proline-rich, 14-kDa NS protein (VP3) was shown to cause apoptosis in lymphoblastoid T cells, and was implicated in pathogenesis (Noteborn, M. H. M., et al.,1994, A single chicken anemia virus protein induces apoptosis. J. Virol. 68, 346–351). However, this protein was found to be essential for viral replication. Similarly, in infectious bursal disease virus (IBDV), another member of the Birnaviridae family, segment A also encodes a 17 kDa NS protein (from a small ORF) which is found in IBDV-infected cells (Mundt, E., J. Beyer, and H. Müller. 1995, Identification of a novel viral protein in infectious bursal disease virus-infected cells. J. Gen. Virol. 76:437–4435). Recently, it was shown that this NS protein of IBDV is not required for viral replication but plays an important role in pathogenesis (U.S. patent application Ser. No. 08/940,968). The present inventors have shown that NS protein of IBDV is not required for viral replication in vitro or in vivo. In addition, the results indicate that IBDV-induced cell death is significantly reduced due to the absence of NS protein expression.

In the absence of NS protein expression, the mutant virus is expected to be attenuated. However, this should not affect the immune response to IPNV in the natural host. Using the present invention, it is possible to prepare novel, live-attenuated vaccines for IPNV, which are nonpathogenic.

DETAILED DESCRIPTION OF THE INVENTION

Synthetic transcripts derived from cloned DNA corresponding to the entire genome of a segmented dsRNA animal virus have been demonstrated to give rise to a replicating virus. The recovery of infectious virus after transfecting cells with synthetic plus-sense RNAs derived from cloned cDNA of a virus with a dsRNA genome completes the quest of generating reverse infectious systems for RNA viruses. A number of investigators have generated infectious animal RNA viruses from cloned cDNA (Boyer, J. C., et al., *Virology*, 198, 415–426 (1994)). Racaniello and Baltimore were first to rescue poliovirus, a plus-stranded RNA virus, using cloned cDNA (Racaniello, V. R. & Baltimore, D. (1981) Science 214, 916–919). Later, van der Werf et al. generated infectious poliovirus using synthetic RNA produced by T7 RNA polymerase on a cloned cDNA template ((van der Werf, S., et al., *Proc. Natl. Acad. Sci. USA*, 83, 2330–2334 (1986)). Enami et al. rescued influenza virus, a segmented negative-stranded RNA virus (Enami, M., et al., *Proc. Natl. Acad. Sci. USA*, 87, 3802–3805 (1990)); and Schnell et al. generated rabies virus, a nonsegmented negative-stranded RNA virus, from cloned cDNAs of their respective genomes (Schnell, M. J., et al., *EMBO J.*, 13, 4195–4205 (1994)). Chen et al. demonstrated that the electroporation of fungal spheroplasts with synthetic plus-sense RNA transcripts, which correspond to the non-segmented dsRNA hypovirus, an uncapsidated fungal virus, yield mycelia that contain cytoplasmic-replicating dsRNA (Chen, B. Choi, G. H. & Nuss, D. L. (1994) Science 264, 1762–1764). Roner et al. developed an infectious system for a segmented dsRNA reovirus by transfecting cells with a combination of ssRNA, dsRNA, in vitro translated reovirus products, and complemented with a helper virus of different serotype (Roner, M. R., Sutphin, L. A. & Joklik, W. K. (1990) *Virology* 179, 845–852). The resulting virus was discriminated from the helper virus by plaque assay. However, in this system the use of a helper virus was necessary. In contrast, the described reverse genetics system of IPNV does not require a helper virus or other viral proteins. Transfection of cells with plus-sense RNAs of both segments was sufficient to generate infectious virus (IPNV). In this regard, the system was comparable to other rescue systems of plus-stranded poliovirus and double-stranded hypovirus (van der Werf, S., et al.(1986) *Proc. Natl. Acad. Sci. USA* 83, 2330–2334; Chen, B., et al. (1994) Science 264,1762–1764).

Transfection of plus-sense RNAs from both segments into the same cell was necessary for the successful recovery of IPNV. Transfected RNAs of both segments had to be translated by the cellular translation machinery. The polyprotein of segment A is presumably processed into NS protease and VP2 and VP3 proteins, which form the viral capsid. The translated protein VP1 of segment B acts as a RNA-dependent RNA polymerase and transcribes minus-strands from synthetic plus-strands of both segments, and the reaction products form dsRNA. Dobos reported that in vitro transcription by the virion RNA-dependent RNA polymerase of IPNV, is primed by VP1 and then proceeds via an asymmetric, semiconservative, strand-displacement mechanism to synthesize only plus strands during replication of the viral genome (Dobos, P. (1995) *Virology* 208, 10–25). The present inventors' system shows that synthesis of minus strands must proceed on the plus strands. Whether the resulting transcribed minus-strand RNA serves as a template for the transcription of plus-strands or not remains the subject of further investigations.

To unequivocally prove that the infectious virus (IPNV) contained in supernatants of transfected cells was indeed derived from the synthetic transcripts, one recombinant virus was generated containing sequence tags in segment B. Restriction enzyme digests of the RT-PCR products and sequence analysis of the cloned DNA fragments are used to verify the presence of these sequence tags in the genomic RNA segments.

The recovery of infectious virus (IPNV) demonstrates that only the plus-strand RNAs of both segments are sufficient to initiate replication of dsRNA. Thus, the results are in agreement with the general features of reovirus and rotavirus replication, where the plus-strand RNAs serve as a template for the synthesis of progeny minus strands to yield dsRNA (Schonberg, M., et al. (1971) Proc. Natl. Acad. Sci. USA 68, 505–508; Patton, J. T. (1986) Virus Res. 6, 217–233; Chen, D., et al., (1994) J. Virol. 68, 7030–7039). However, the semiconservative strand displacement mechanisms proposed by Spies et al. and Dobos could not be excluded (Spies, U., et al. (1987) Virus Res. 8, 127–140; Dobos, P. (1995) Virology 208, 10–25). The development of a reverse genetics system for IPNV will greatly facilitate future studies of gene expression, pathogenesis, and help in the design of a new generation of live IPNV vaccines.

In order to study the function of the 15–17 kDa nonstructural (NS) protein in viral growth and pathogenesis, a cDNA clone of IPNV segment A is constructed, in which the NS protein is mutated to prevent expression. Segment A is preferably mutated in more than one region to prevent the expression of NS protein. Mutation in more than one region of the NS protein is preferable to lower the chances of a reversion to the wild type strain.

Transfection of cells with combined transcripts of either modified or unmodified segment A along with segment B will produce viable IPN viruses. When transfectant viruses are characterized by immunofluorescence assays using NS-specific antiserum, a lack of NS protein expression is characterized by lack of a fluorescence signal. Furthermore, replication kinetics and cytotoxic effects of the mutant virus can be compared with that of the wild type (WT) virus in vitro. The mutant virus will exhibit decreased cytotoxic effects in cell culture.

To evaluate the characteristics of the recovered viruses in vivo, chinook salmon were inoculated with WT or mutant virus and analyzed for histopathological lesions. The WT virus caused microscopic lesions in the pancreas while the mutant virus failed to show any pathological lesions or clinical signs of disease. In both instances, the virus can be recovered from the pancreas and the presence or absence of mutation in the recovered viruses confirmed by nucleotide sequence analysis of the NS gene.

A mutant cDNA clone of segment A of the SP strain of IPNV was constructed in which the first initiation codon of the NS gene was mutated to prevent expression of the NS protein and to study the role of NS protein in IPNV. Thus, the resulting plasmid encodes only the precursor of the structural proteins (VP2, NS protease, and VP3). In addition, a full-length cDNA clone of segment B of the SP strain of IPNV is constructed, which encodes VP1 protein.

Chinook salmon embryo (CHSE) cells were transfected with combined transcripts of segments A and B to study the function of NS protein in viral replication. To verify the mutation in the resulting virus, the genomic RNA was isolated and analyzed by reverse transcription polymerase chain reaction (RT-PCR) using a primer pair specific for segment A. Sequence analysis of the cloned PCR product was used to confirm the expected nucleotide mutations in the NS gene from the mutant virus.

CHSE cells can be infected with the recovered viruses and analyzed by immunofluorescence assay using NS-specific antiserum to detect the expression of NS protein. Cells expressing NS protein give a positive immunofluorescence signal. However, cells in which expression of NS protein is prevented fail to give any fluorescence signal. NS protein is not required for replication in cell culture.

In order to determine the replication kinetics of the virus, CHSE cells are infected with unmodified and NS deficient virus and their titers are determined by plaque assay.

Furthermore, the transfectant viruses are purified by CsCl gradient, and their proteins are analyzed by Western blot analysis using IPNV antiserum. Qualitatively, viral structural proteins (VP2, and VP3) produced by the mutant virus should be identical to the proteins synthesized by the unmodified virus.

The viruses were propagated in CHSE cells, whole cell nucleic acids was isolated and the NS gene amplified by RT-PCR to determine the genetic stability of the transfectant viruses in vitro. Sequence analysis of the cloned PCR product was used to confirm the expected nucleotide mutations in the NS gene of the mutant virus. Similarly, to determine the genetic stability of these viruses in vivo, chinook salmon can be inoculated with transfectant viruses, and their pancreatic tissue collected at various days post-infection. Total nucleic acid is extracted from the pancreatic tissue, and the NS gene amplified by RT-PCR using a primer pair specific for segment A. This assay demonstrates that the mutant virus can replicate in the pancreas of the chinook salmon but do not revert to the wild-type IPNV.

Chinook salmon can be inoculated with equal amounts of modified and unmodified IPNV to compare the replication behavior of recovered viruses in vivo. Virus titers in the pancreatic tissue from each group at different time points are determined by plaque assay on CHSE cells. Indirect IFA can be performed on pancreatic tissue of the salmon infected with mutant IPNV, using NS-specific antiserum to confirm the lack of NS protein expression. This will show that the mutant virus, lacking the expression of NS protein, efficiently replicate in the pancreatic tissue of salmon.

To compare the immune response induced by the unmodified and mutated IPNV, salmon can be innoculated with the mutant and unmodified viruses, bled, and their sera analyzed by virus neutralization (VN) test. This assay will show that the mutant virus, which is deficient in producing NS protein, does not affect the immune response to IPNV in the natural host.

As used in the present application, the term "synthetic" as applied to nucleic acids indicates that it is a man made nucleic acid in contrast to a naturally occurring nucleic acid. The term implies no limitation as to the method of manufacture, which can be chemical or biological as long as the method of manufacture involves the intervention of man.

The term "cDNA" is intended to encompass any cDNA containing segments A and B and the 5' and 3' noncoding regions of segments A and B.

The term "infectious" as applied to viruses indicates that the virus has the ability to reproduce. The virus can be pathogenic or nonpathogenic and still be infectious.

The term "aquatic Birnavirus" is intended to encompass any Birnavirus which infects marine or freshwater organisms such as fish, shrimp and other crustaceans, oysters and other mollusks.

The present invention provides a system for the generation of NS protein deficient infectious pancreatic necrosis virus using synthetic RNA transcripts. This system can be used to study pathogenesis and for the design of a new generation of live and inactivated IPNV vaccines.

The present invention provides a recombinant vector containing at least one copy of the cDNA according to the present invention. The recombinant vector may also comprise other necessary sequences such as expression control sequences, markers, amplifying genes, signal sequences, promoters, and the like, as is known in the art. Useful vectors for this purpose are plasmids, and viruses such as baculoviruses, herpes virus of fish (channel catfish virus), and the like.

Also provided herein is a host cell transformed with the recombinant vector of the present invention or a host cell transfected with the synthetic RNA of the present invention. The host cell may be a eukaryotic or a prokaryotic host cell. Suitable examples are E. coli, insect cell lines such as Sf-9, Chinook salmon embryo (CHSE) cells, Rainbow trout gonad (RTG-2) cells, Bluegill fish (BF-2) cells, Brown Bullhead (BB) cells, Fathead Minnow (FHM) cells, and the like.

Also part of this invention is an NS protein deficient IPNV vaccine comprising a protecting amount of a recombinantly produced virus or portion of a virus, wherein the virus does not induce pathological lesions.

The virus can be further modified or inactivated by chemical or physical means. Chemical inactivation can be achieved by treating the virus with, for example, enzymes, formaldehyde, β-propiolactone, ethylene-imine or a derivative thereof, an organic solvent (e.g. halogenated hydrocarbon) and or a detergent. If necessary, the inactivating substance can be neutralized after the virus has been inactivated. Physical inactivation can be carried out by subjecting the viruses to radiation such as UV light, X-radiation, or y-radiation.

The virus can also be modified by known methods including serial passage, deleting further sequences of nucleic acids and site directed. mutagenesis either before or after production of the infectious virus.

The virus can be a chimeric recombinant virus which contains epitopic determinants for more than one strain of IPNV. Epitopic determinants as discussed in the present document are amino acids or amino acid sequences which correspond to epitopes recognized by one or more monoclonal antibodies. Since VP2 protein is the major host protective immunogen of IPNV, the chimeric virus could include a portion of VP2 immunogens from at least two different IPNV strains in addition to the modified NS gene according to the present invention. Methods for producing a chimeric virus are disclosed in Vakharia, *Biotechnology Annual Review* Volume 3, 151–168, 1997; Snyder et al., *Avian Diseases*, 38:701–707, 1994; and WO 95/26196. Strains suitable for use in producing a chimeric IPN virus include but are not limited to West Buxton, Jasper, SP, N1, DRT, Ab, HE, and TE strains.

Physiologically acceptable carriers for vaccination of fish are known in the art and need not be further described herein. In addition to being physiologically acceptable to the fish the carrier must not interfere with the immunological response elicited by the vaccine and/or with the expression of its polypeptide product.

Other additives, such as adjuvants and stabilizers, among others, may also be contained in the vaccine in amounts known in the art. Preferably, adjuvants such as aluminum hydroxide, aluminum phosphate, plant and animal oils, and the like, are administered with the vaccine in amounts sufficient to enhance the immune response to the IPNV. The amount of adjuvant added to the vaccine will vary depending on the nature of the adjuvant, generally ranging from about 0.1 to about 100 times the weight of the IPNV, preferably from about 1 to about 10 times the weight of the IPNV.

The vaccine of the present invention may also contain various stabilizers. Any suitable stabilizer can be used including carbohydrates such as sorbitol, mannitol, starch, sucrose, dextrin, or glucose; proteins such as albumin or casein; and buffers such as alkaline metal phosphate and the like. A stabilizer is particularly advantageous when a dry vaccine preparation is prepared by lyophilization.

The vaccine can be administered by any suitable known method of inoculating fish including but not limited to immersion, oral administration, spraying and injection. Preferably, the vaccine is administered by mass administration techniques such as immersion. When administered by injection, the vaccines are preferably administered parenterally. Parenteral administration as used herein means administration by intravenous, subcutaneous, intramuscular, or intraperitoneal injection.

The vaccine of the present invention is administered to fish to prevent IPNV anytime before or after hatching. The term "fish" is defined to include but not be limited to fish species including trout, salmon, carp, perch, pike, eels, and char as well as mollusks and crustaceans.

The vaccine may be provided in a sterile container in unit form or in other amounts. It is preferably stored frozen, below −20° C., and more preferably below −70° C. It is thawed prior to use, and may be refrozen immediately thereafter. For administration to fish, the recombinantly produced virus may be suspended in a carrier in an amount of about $10^2$ to $10^7$ pfu/ml, and more preferably about $10^5$ to $10^6$ pfu/ml in a carrier such as a saline solution. The inactivated vaccine may contain the antigenic equivalent of $10^4$ to $10^7$ pfu/ml suspended in a carrier. Other carriers may also be utilized as is known in the art. Examples of pharmaceutically acceptable carriers are diluents and inert pharmaceutical carriers known in the art. Preferably, the carrier or diluent is one compatible with the administration of the vaccine by mass administration techniques. However, the carrier or diluent may also be compatible with other administration methods such as injection, and the like.

The invention also can be used to produce combination vaccines with the IPNV material. The IPNV material can be combined with antigen material of other relevant fish pathogens and/or bacterial antigens. Examples of relevant fish pathogens include but are not limited to infectious hematopoietic necrosis virus (IHNV), viral hemorrhagic septicemia virus (VHSV), ISAV (Infectious salmon anemia virus), PDV (Pancreas disease virus), Irido virus and Nodavirus. Examples of relevant bacterial antigens include but are not limited to antigens from gram positive bacteria such as but not limited to Lactococcus garvieae and gram negative bacteria such as but not limited to Aeromonas salmonicida. Other relevant bacterial antigens include but but are not limited to antigens from Vibrio anguillarum, Vibrio salmonicida, Vibrio viscosus, Yersinia ruckri, Piscirickettsia salmonis, Renibacterium salmoninarum, Pasturella piscicida, Flavobacterium columnare, and Flavobacterium psychrophilum.

The foregoing embodiments of the present invention are further described in the following Examples. However, the present invention is not limited by the Examples, and variations will be apparent to those skilled in the art without departing from the scope of the present invention.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 3a and 3b. Nucleotide sequence comparison of the 5'- and 3'-noncoding regions of segments A (A) and (B) of IPNV strains Jasper (JAS), SP, and West Buxton (WB). The start and stop codons of segments A and B major open reading frames of both strains are in bold. Nucleotide differences between the two strains are marked and nucleotide identity is marked by (–). Nucleotide deletions in WB and Sp strains are marked, and an additional C residue at the 3'-end of WB and Sp segment A is indicated. Invert terminal repeats in segment A and B of both strains are blocked and italicized (SEQ ID NO. 44–47).

EXAMPLES

Example 1

Figure 1:
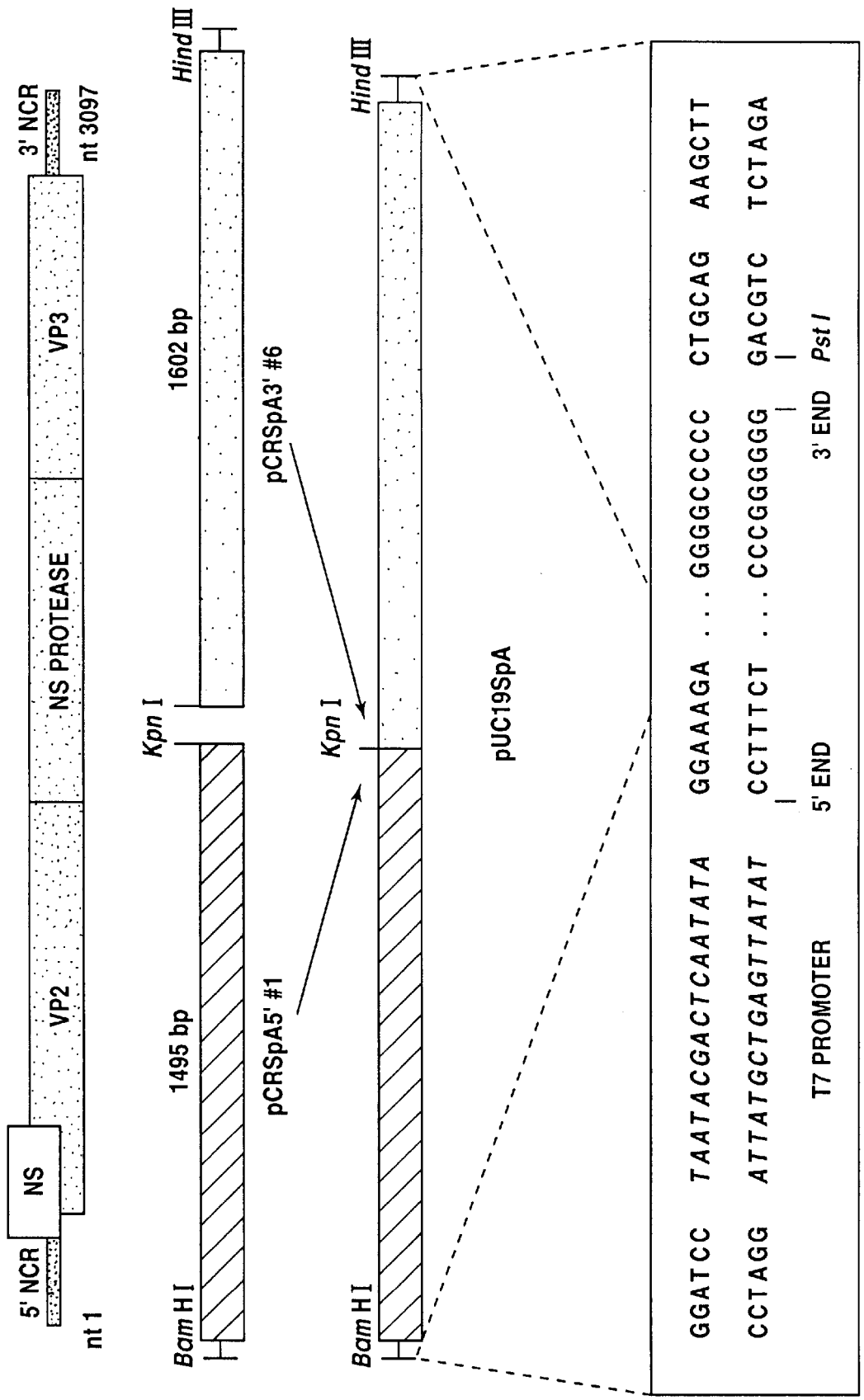
FIG. 1. Construction of the full-length cDNA clone of IPNV segment A for the generation of plus-sense RNA transcript with T7 RNA polymerase. The gene structure of IPNV segment A and its encoded proteins are shown at the top. Overlapping cDNA segments of IPNV were generated by RT-PCR and cloned into a pCR2.1 vector to obtain various pCR clones, as indicated. These plasmids were digested with appropriate restriction enzymes, and the resulting segments were then cloned into a pUC19 vector to obtain plasmid pUC19SpA. This plasmid contains a T7 RNA polymerase promoter sequence at its 5'-end. Restriction enzymes used for the construction or linearization of the full-length clone are indicated (SEQ ID NO. 40,41).

Generation of Infectious Virus from Synthetic RNAs

Cells and viruses. CHSE-214 cells (ATCC, CRL-1681) were maintained at room temperature in minimum essential medium containing Hank's salts, and supplemented with 10% fetal bovine serum (FBS). These cells were used for propagation of IPNV, transfection experiments, further propagation of the recovered virus and immunofluorescence studies, essentially as described earlier (Mundt, E., and V. N. Vakharia. 1996, Synthetic transcripts of double-stranded birnavirus genome are infectious. Proc. Natl. Acad. Sci. USA 93:11131–11136). The West Buxton (WB) strain of IPNV (a reference serogroup A1 strain) was kindly provided by Frank M. Hetrick (Maryland Department of Agriculture, College Park, Md.), and purified as described previously with slight modification (Chang, N., R. D. MacDonald, and T. Yamamoto, 1978, Purification of infectious pancreatic necrosis (IPN) virus and comparison of peptide composition of different isolates, Can. J. Microbiol. 24:19–27). Briefly, CHSE cells were infected with IPNV and after the cytopathic effect was visible, the cells were scraped into the medium and the crude virus was clarified by centrifugation at 5,000×g for 30 min at 4° C. The pellet was resuspended in 10 ml of TNE buffer (0.1 M Tris-HCl, pH7.4, 0.1 M NaCl, 1 mM EDTA), mixed with 1 volume of Freon and homogenized for 5 min. After centrifugation at 8,000×g for 20 min at 4° C., the aqueous layer was aspirated and mixed with the supernatant of the crude virus preparation. Polyethylene glycol (PEG, 20,000 MW) was added to a final concentration of 10% (w/v) and the mixture was incubated overnight at 4° C. The solution was centrifuged at 8,000×g for 30 min 4° C. to pellet the virus which was resuspended in 10 ml of TNE buffer. After Freon extraction, the virus was pelleted at 100,000×g for 1.5 h at 4° C. and resuspended in 0.5 ml of TNE buffer. The virus was layered onto a cushion of 30% sucrose (w/v, in TNE buffer) and centrifuged at 120,000×g for 1 h at 4° C. Finally, the virus pellet was resuspended in 100 μl of TNE buffer and stored at −20° C. until use.

Determination of 5' and 3' termini of the IPNV genome. Complete nucleotide sequences of 5'- and 3'-noncoding regions of both genome segments of IPNV were determined by two methods as described for IBDV (Mundt, E., and H. Müller. 1995. Complete nucleotide sequences of 5'- and 3'-noncoding regions of both genome segments of different strains of infectious bursal disease virus. Virology 209:10–18). Briefly, viral RNA was isolated from purified virus by digesting with proteinase K (200 μg/ml final concentration) for 6 hr at 37° C. in the presence of sodium dodecyl sulfate (1%) followed by phenol/chloroform extraction and ethanol precipitation (Sambrook, J., E. F. Fritsch, and T. Maniatis. 1989. Molecular Cloning a laboratory manual.2nd ed. Cold Spring Harbor Laboratory. Cold Spring Harbor. N.Y.). To determine the 3' termini of both strands of segments A and B, the viral RNA was polyadenylated, reverse transcribed with either A-A3'F, A-A5'R, B-B3'F or B-B5'R primer (Table 1), and the resulting cDNA amplified by PCR using a poly-dT primer (5'-GCGGCCGCCCTTTTTTTTTTTTTTTT-3'(SEQ ID NO. 1)) (Cashdollar, L. W., J. Esparza, J. R. Hudson, R. Chmelo, P. W. K. Lee, and W. K Joklik. 1982. Cloning of double-stranded RNA genes of reovirus. Sequences of the cloned S2 gene. Proc. Natl. Acad. Sci. USA 79:7644–7648). The reverse transcription (RT)-PCR products were separated by agarose gel electrophoresis, purified by QIAquick gel extraction kit (Qiagen, Inc.) and directly sequenced by the dideoxy chain termination method (Sanger, F., S. Nicklen, and A. R. Coulson. 1977. DNA sequencing with chain-terminating inhibitor. Proc. Natl. Acad Sci USA 74:5463–5467), using the segment-specific primers described above. The 5' termini of segments A and B were determined by rapid amplification of cDNA ends using the 5' RACE system (GIBCO/BRL) (Frohman, M. A., M. K. Dush, and G. R. Martin. 1988. Rapid production of full-length cDNA rare transcripts: Amplification using a single gene-specific oligonucleotide primer. Proc. Natl. Acad. Sci USA 85:8998–9002). Briefly, the cDNA of segments A and B was synthesized by RT reaction using virus-specific primers A-ApaR and B-HindR (Table 1), respectively. The cDNA was purified by chromatography on GlassMAX columns and tailed with oligo-dC using terminal deoxynucleotidyltransferase. The tailed cDNA was amplified by PCR using nested virus-specific primer A-A5'R or B-B5'R (Table 1) and abridged anchor primer, according to the manufacturer's protocol. The PCR products were gel-purified and directly sequenced using segment-specific primers, as described above.

Construction of full-length genomic cDNA clones of IPNV. The cDNA clones containing the entire coding and noncoding regions of IPNV-RNA segments A and B were prepared using standard cloning procedures and methods, as described for IBDV (Mundt, E., and V. N. Vakharia. 1996, Synthetic transcripts of double-stranded birnavirus genome are infectious. Proc. Natl. Acad. Sci. USA 93:11131–11136). In addition, all manipulations of DNAs were performed according to standard protocols (Sambrook, J., E. F. Fritsch, and T. Maniatis. 1989. Molecular Cloning a laboratory manual.2nd ed. Cold Spring Harbor Laboratory. Cold Spring Harbor. N.Y.). On the basis of published IPNV sequences of the Jasper strain and the determined 5'- and 3'-terminal sequences of the WB strain, several primer pairs were synthesized and employed in RT-PCR amplifications (see Table 1).

Figure 6:
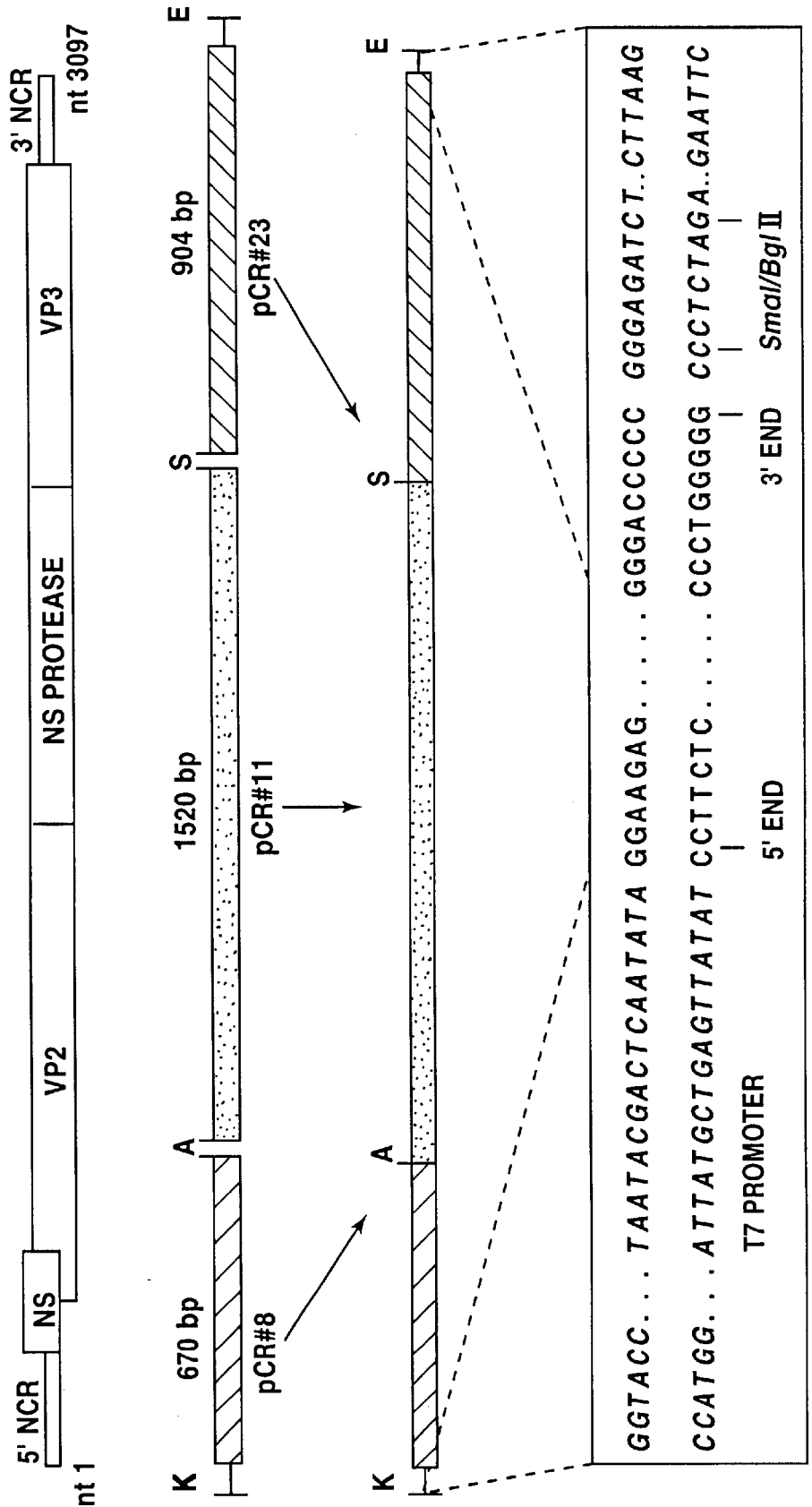
FIG. 6. Construction of the full-length cDNA clone of IPNV segment A for the generation of plus-sense RNA transcript with T7 RNA polymerase. The gene structure of IPNV segment A and its encoded proteins are shown at the top. Overlapping cDNA segments of IPNV were generated by RT-PCR and cloned into a pCR2.1 vector to obtain various pCR clones, as indicated. These plasmids were digested with appropriate restriction enzymes, and the resulting segments were then cloned into a pUC19 vector to obtain plasmid pUC19WBA. This plasmid contains a T7 RNA polymerase promoter sequence at its 5'-end. Restriction enzymes used for the construction or linearization of the full-length clone are indicated. Abbreviations: A. ApaI: E. EcoRI: K. Asp718: S.SalI (SEQ ID NO. 48,49).
Figure 7:
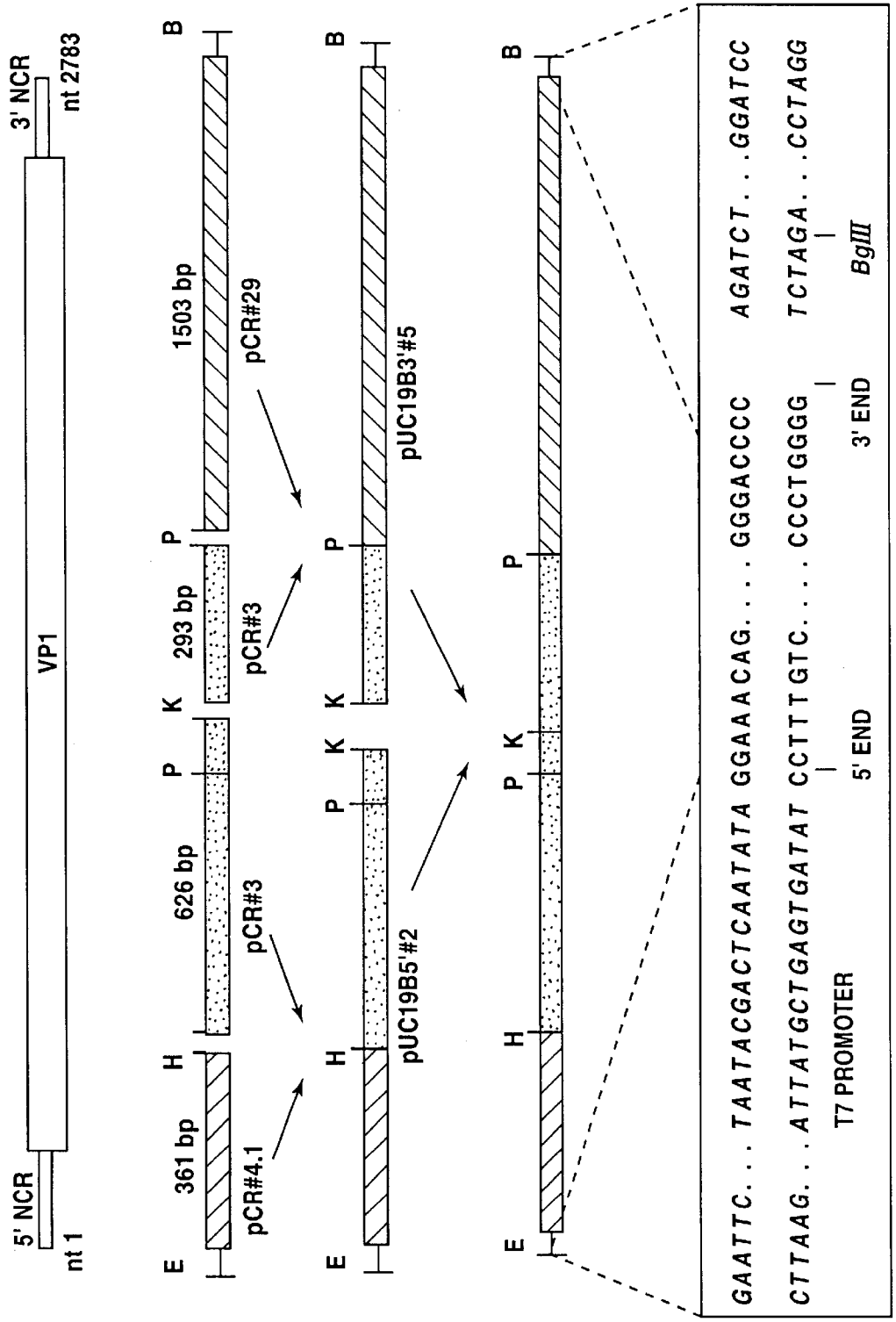
FIG. 7. Construction of the full-length cDNA clone of IPNV segment B for the synthesis of plus-sense RNA transcript with T7 RNA polymerase. The genome segment B of IPNV encodes the RNA-dependent RNA polymerase, VP1, which is shown at the top. Overlapping cDNA segments of IPNV were cloned into a pCR2.1 vector to obtain various pCR clones, as shown. These plasmids were digested with appropriate restriction enzymes, and the resulting segments were then cloned into a pUC19 vector to obtain plasmids pUC19B5'#2 and pUC19B3'#5. Finally, a full-length plasmid pUC18WBB was obtained from these two clones, which contains a T7 RNA polymerase promoter sequence at its 5'-end. Restriction enzymes used for the construction of the above plasmids or linearization of the full-length clone are indicated. Abbreviations: B. BamHI: E. EcoRI: H. HindIII: K. Asp718: P.PstI (SEQ ID NO. 50,51).
Figure 8:
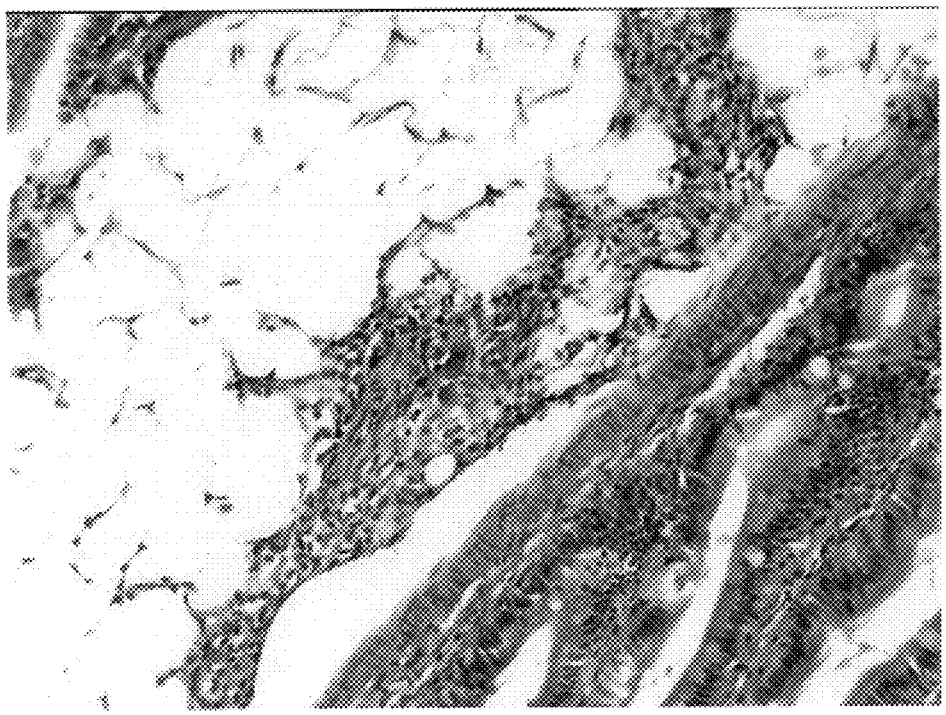
FIG. 8. Atlantic salmon fry, exocrine pancreas, infected with a 2nd passage of a virulent isolate of IPNV (serotype Sp), 8 days post infection. Pyloric caecae to the lower left. Exocrine tissue has almost disappeared with only a few exocrine cells remaining. Moderate inflammatory reaction.
Figure 9:
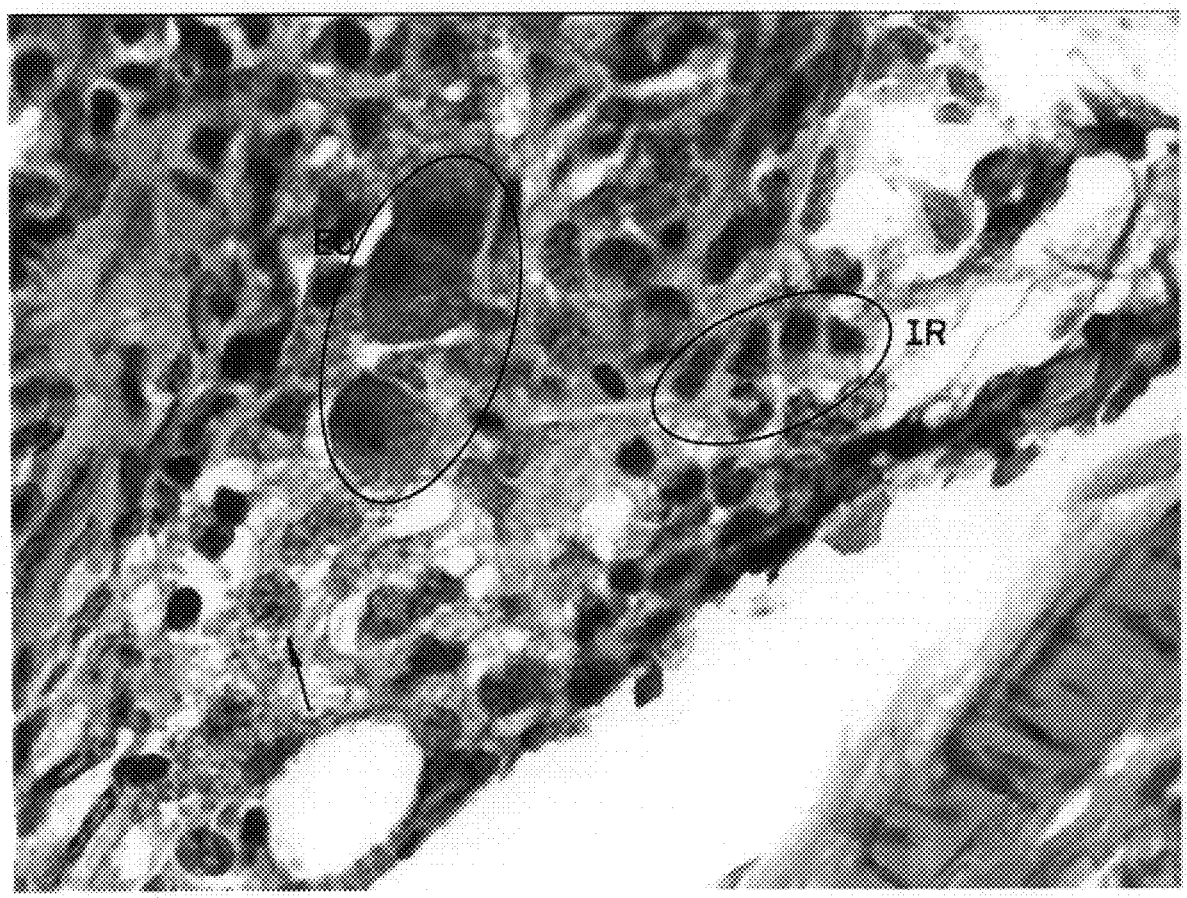
FIG. 9. Atlantic salmon fry, exocrine pancreas, infected with a 2nd passage of a virulent isolate of IPNV (serotype Sp), 8 days post infection. Close up of FIG. 8 showing a few remaining exocrine cells (EC), indistinct cell borders (degenerate cells) with released zymogen granules (arrow). Minor inflammatory reaction (IR).
Figure 10:
FIG. 10. Atlantic salmon fry, exocrine pancreas, infected with IPNV mutant (serotype Sp), 8 days post infection. Transversely sectioned pyloric caecae with exocrine pancreas loacted between the caecae. No histomorphological changes observed in exocrine tissue.
Figure 11:
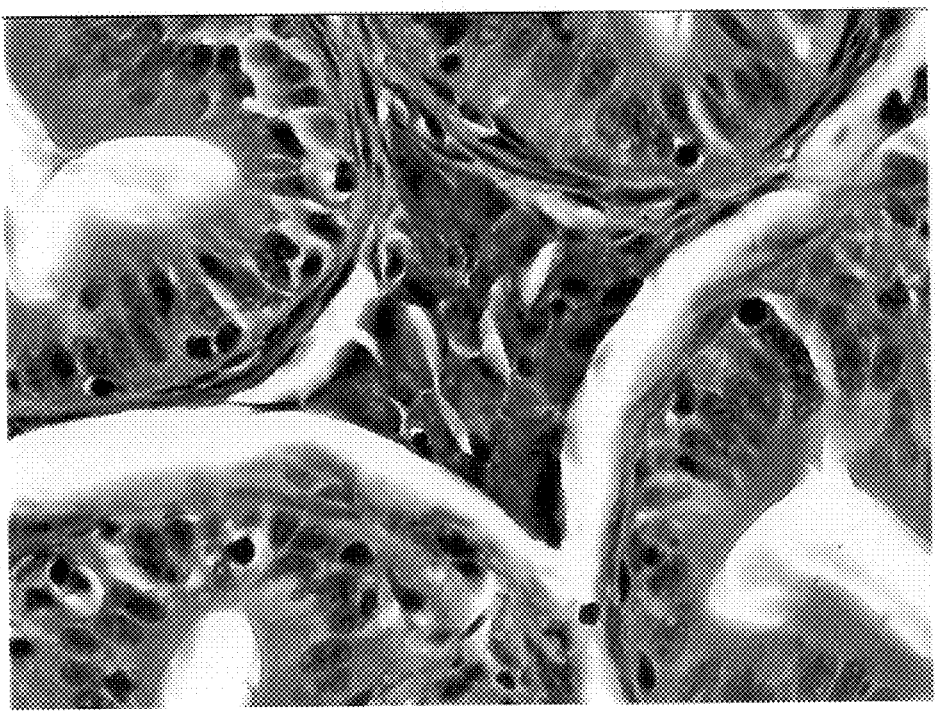
FIG. 11. Atlantic salmon fry, exocrine pancreas, infected with IPNV mutant (serotype Sp), 8 days post infection. Higher magnification of FIG. 3 with transversly sectioned pyloric caecae. The exocrine pancreas has a normal appearance with no histomorphological signs of degeneration.

To generate cDNA clones of segment A of WB strain, three primer pairs (A-A5'NC plus A-ApaR, A-ApaF plus A-SalR, and A-SalF plus A-A3'NC) were used for RT-PCR amplification (Table 1). Using genomic RNA as a template, desired overlapping cDNA fragments of segment A were synthesized and amplified according to the supplier's protocol (Perkin-Elmer). Amplified fragments were cloned into the EcoRI site of a pCR2.1 vector (Invitrogen Corp.) to obtain plasmids pCR#8, pCR#11, and pCR#23, respectively (FIG. 6). The insert DNA in all these plasmids was sequenced by the dideoxy chain termination method (Sanger, F., S. Nicklen, and A. R. Coulson, 1977, DNA sequencing with chain-terminating inhibitor. Proc. Natl. Acad Sci USA 74:5463–5467), using an Applied Biosystem automated DNA sequencer, and the sequence data were analyzed by using PC/GENE (Intelligenetics) software. To construct a full-length cDNA clone of segment A, plasmids pCR#8, pCR#11, and pCR#23 were double-digested with restriction enzyme pairs Asp 718 plus ApaI, ApaI plus SalI, and SalI plus EcoRI to release 670, 1520, and 904 bp fragments, respectively. These fragments were then cloned between the EcoRI and Asp 718 sites of pUC19 vector to obtain plasmid pUC19WBA. This plasmid contains a full-length copy of segment A, which encodes all of the structural and nonstructural proteins (FIG. 6). Similarly, to prepare cDNA clones of segment B, three primer pairs (B-B5'NC plus B-HindR, B-HindF plus B-PstR, and B-PstF plus B-Bgl3'NC) were used to generate overlapping cDNA fragments of segment B by RT-PCR amplification (Table 1). Amplified fragments were cloned into pCR2.1 vector as above to obtain plasmids pCR#4.1, pCR#3, and pCR#29, respectively (FIG. 7). DNA from these plasmids was sequenced and analyzed as described above. Since sequence analysis of plasmid pCR#3 revealed an internal PstI site, it was necessary to make two additional plasmids. To construct these clones (pUC19B5'#2 and pUC19B3'#5), plasmids pCR#4.1, pCR#3, and pCR#29 were double-digested with enzyme pairs EcoRI plus HindIII, HindIII plus Asp 718 or Asp 718 plus PstI, and PstI plus BamHI. After these digestions, respective fragments of 361, 626 or 293, and 1503 bp were released. The EcoRI—HindIII and HindIII—Asp 718 fragments were first cloned between the EcoRI—Asp 718 sites of pUC19 vector to obtain plasmid pUC19B5'#2. Then the Asp 718—PstI and PstI—BamHI fragments were cloned between the Asp 718 and BamHI sites of pUC19 vector to obtain plasmid pUC19B3'#5. Finally, to construct a full-length cDNA clone of segment B, plasmid pUC19B3'#5 was digested with Asp 718 and BamHI and the resultant fragment was cloned into the Asp 718—BamHI digested pUC19B5'#2 vector. A representative clone of segment B was selected and designated pUC19WBB, which encodes VP1 protein (FIG. 7).

To introduce a sequence tag into IPNV segment B, plasmid pUC19WBBmut was constructed by oligonucleotide-directed mutagenesis using specific primer pairs and PCR amplification of the parent plasmid pUC19WBB. To construct pUC19WBBmut, two primer pairs (B-SacF plus B-Sma(R and B-Sma(F plus B-BstR; see Table 1) were synthesized and used to amplify the DNA fragments of 568 and 407 bp, respectively. These fragments were combined and subsequently amplified by PCR using the flanking primers (B-SacF plus B-BstR) to produce a 954-bp fragment. This fragment was digested with SacII and BstEII enzymes, and the resulting fragment (798 bp) was cloned back into SacII—BstEII-cleaved parent plasmid pUC19WBB. As a result of this mutation, the unique internal SmaI site in this plasmid was deleted. Another plasmid, pUC19WBB-Sma, was constructed which after linearization with a SmaI enzyme and transcription reaction would yield a RNA transcript with precise 3'-end sequences as the genomic RNA. To construct this plasmid, primer pairs (B-BstF plus B-Sma3'NC; see Table 1) were synthesized and used to amplify a 723-bp fragment by PCR from pUC19WBmut template. The amplified fragment was digested with BstEII and BglII enzymes, and the resulting fragment (584 bp) was cloned back into the same sites of this plasmid. Finally, a representative clone of segment B was selected and designated pUC19WBB-Sma, which lacked an internal SmaI site.

The integrity of the full-length constructs, pUC19WBA, pUC 19WBB and pUC19WBB-Sma, was tested by in vitro transcription and translation coupled reticulocyte lysate system using T7 RNA polymerase (Promega Corp.).

Transcription and transfection of synthetic RNAs. Transcription and transfection assays were performed as described in detail previously (Mundt, E., and V. N. Vakharia. 1996, Synthetic transcripts of double-stranded birnavirus genome are infectious. Proc. Natl. Acad. Sci. USA 93:11131–11136), except CHSE cells were used for transfection. Briefly, plasmid pUC19WBA was digested with SmaI, and plasmids pUC19WBB and pUC19WBB-Sma were digested with BglII and SmaI enzymes, respectively (FIGS. 6 and 7). These linearized plasmids were used as templates for in vitro transcription with T7 RNA polymerase (Promega Corp.). CHSE cells were transfected with combined plus-sense transcripts derived from plasmids pUC19WBA and pUC19WBB or pUC19WBA and pUC19WBB-Sma, using Lipofectin reagent (GIBCO/BRL). The resulting virus progeny were designated recombinant WB (rWB) and rWB-Sma, respectively.

Characterization of recovered IPNV. To determine the specificity of the recovered viruses, CHSE cells were infected with the supernatants of rWB or rWB-Sma IPNV and the infected cells were analyzed by immunofluorescence assay (IFA) using rabbit anti-IPNV polyclonal serum. The anti-IPNV serum, prepared against the Jasper strain of serogroup A, was kindly provided by Ana Baya (VA-MD Regional College of Veterinary Medicine, College Park, Md.). CHSE cells, grown on cover slips to 80% confluence, were infected with the supernatants of rWB or rWB-Sma IPNV and incubated at room temperature for an appropriate time interval. The cells were then washed with phosphate-buffered saline, pH 7.4 (PBS), fixed with ice-cold methanol-acetone (1:1), and treated with rabbit anti-IPNV serum. After washing with PBS, the cells were treated with fluorescein labeled goat-anti-rabbit antibody (Kirkegaard & Perry Laboratories) and examined by fluorescence microscopy.

To identify the tagged sequence in recovered viruses, total nucleic acids of uninfected and IPNV-infected CHSE cells were isolated and analyzed by RT-PCR, as described above. Segment B-specific primer B-BstR, binding to nucleotide positions 2285–2305 (Table 1), was used for RT of genomic RNA. Following RT, the reaction products were amplified by PCR using an upstream segment B-specific primer B-SacF (binding to nucleotide positions 1351–1371; see Table 1). The resulting PCR fragments (954-bp) were gel-purified and either sequenced as described previously, or digested with SmaI enzyme to determine the tag sequence.

Sequence analysis of IPNV genome. The complete nucleotide sequence of IPNV genome segments of A and B, including the precise 5'-and 3'-terminal sequences was determined. Segment A is 3097 bp long and contains two overlapping open reading frames (ORF). The major ORF encodes the structural VP2 and VP3 proteins, and NS protease, whereas the minor ORF codes for the nonstructural (NS) protein (FIG. 6). Segment B is 2783 bp long and it encodes VP1, which is the RNA-dependent RNA polymerase (FIG. 7). Comparison of the 5' and 3' terminal sequences of segments A and B of WB strain with the Jasper strain showed some minor differences. For example, in segment A, a deletion of a T residue at nucleotide position 106 and an addition of a C residue at position 3097 was detected, whereas in segment B, a deletion of a C residue was found at position 2646. Comparison of the nucleotide and deduced amino acid sequences of WB strain segments A and B with that of the Jasper strain showed 91.64% and 90.37% identity at the nucleotide level, and 97.22% and 97.16% identity at the amino acid level, respectively. This indicates that these two North American strains of IPNV are closely related.

Construction of full-length cDNA clones. To develop a reverse genetics system for IPNV, we constructed full-length cDNA clones of segments A and B of IPNV strain WB. Plasmid pUC19WBA, upon digestion with SmaI and transcription in vitro by T7RNA polymerase, yielded RNA with precise 5' and 3' ends and it encoded all of the structural and nonstructural proteins (FIG. 6). However, plasmid pUC19WBB after linearization with BgAI and transcription, yielded RNA with the correct 5' end but with an additional 5 nucleotides at the 3' end, and it encoded VP1 protein (FIG. 7). A plasmid pUC19WBB-Sma with a genetic tag (elimination of an internal SmaI site) was also constructed to identify virus as being of recombinant origin. Linearization of this plasmid with SmaI and transcription in vitro yielded RNA with precise 5' and 3' ends. Coupled transcription and translation of the above plasmids in a rabbit reticulocyte system yielded protein products, which co-migrated with the marker IPNV proteins after fractionation on a sodium dodecyl sulfate-12.5% polyacrylamide gel and autoradiography.

Transfection and recovery of IPNV. Plus-sense transcripts of IPNV segments A and B were synthesized separately in vitro with T7 RNA polymerase using linearized plasmids pUC19WBA, pUC19WBB and pUC19WBB-Sma as templates. Synthetic RNA transcript(s) derived from these clones was then used to transfect CHSE cells, as shown in Table 2. The results indicate that the transcripts derived from plasmids pUC19WBA and pUC19WBB were able to generate infectious virus after 12 days post transfection, as evidenced by the appearance of cytopathic effect (CPE). Similarly, transcripts derived from plasmids pUC19WBA and pUC19WBB-Sma, either untreated or treated with DNase, gave rise to infectious virus after 10 days post transfection. No CPE was detected when CHSE cells were transfected with either RNase-treated transcripts of plasmids pUC19WBA and pUC19WBB-Sma or uncapped RNAs of these plasmids or individual RNA of each plasmid or Lipofectin reagent. These results indicate plus-sense RNA transcripts of segments A and B are required for the generation of IPNV, in agreement with the previous findings on IBDV reported from our laboratory (Mundt, E., and V. N. Vakharia. 1996. Synthetic transcripts of double-stranded birnavirus genome are infectious. Proc. Natl. Acad. Sci. USA 93:11131–11136).

Figure 4:
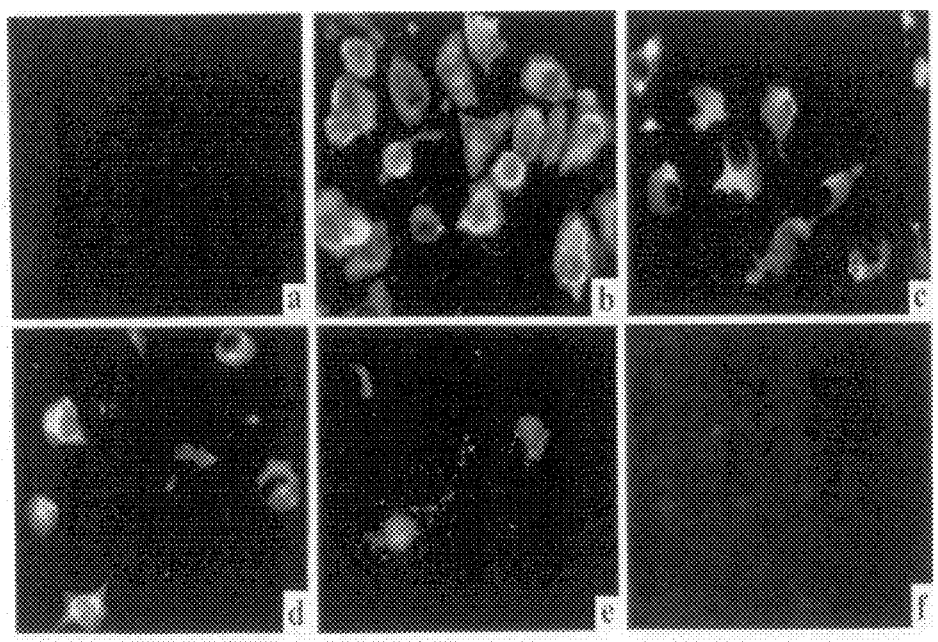
FIGS. 4a–4f. Immunofluorescence staining of IPNV-infected cells for the detection of virus-specific proteins. CHSE cells were infected with the supernatants of recovered IPNVs and harvested at different time intervals. Cells were fixed at 24 h (b), 36 h (c), 48 h (d), 72 h (e) postinfection, and analyzed by immunofluorescence assay using rabbit anti-IPNV polyclonal serum. Uninfected CHSE cells at 24 h (a) and 72 h (f) were used as negative controls. (Magnifications are ×200).

To verify the infectivity of the recovered viruses, transfected CHSE cells were freeze-thawed, and cell-free supernatants were used to infect fresh CHSE cells. After third passage, virus stocks of rWB and rWB-Sma were prepared. The titer of these recovered viruses was comparable to that of the parental WB strain. To determine the specificity of the recovered viruses, CHSE cells were infected with the supernatants of either rWB or rWB-Sma viruses. At various time intervals, the cells were harvested and analyzed by IFA using anti-IPNV polyclonal serum. FIG. 4 shows the results of immunofluorescence staining of IPNV-infected cells. CHSE cells infected with recovered IPNVs gave a positive green immunofluorescence signal, indicating the expression of virus-specific proteins (FIGS. 4b–e). However, no fluorescence was detected in the mock-infected cells at 24 h and 72 h (FIG. 4a and f).

Figure 5:
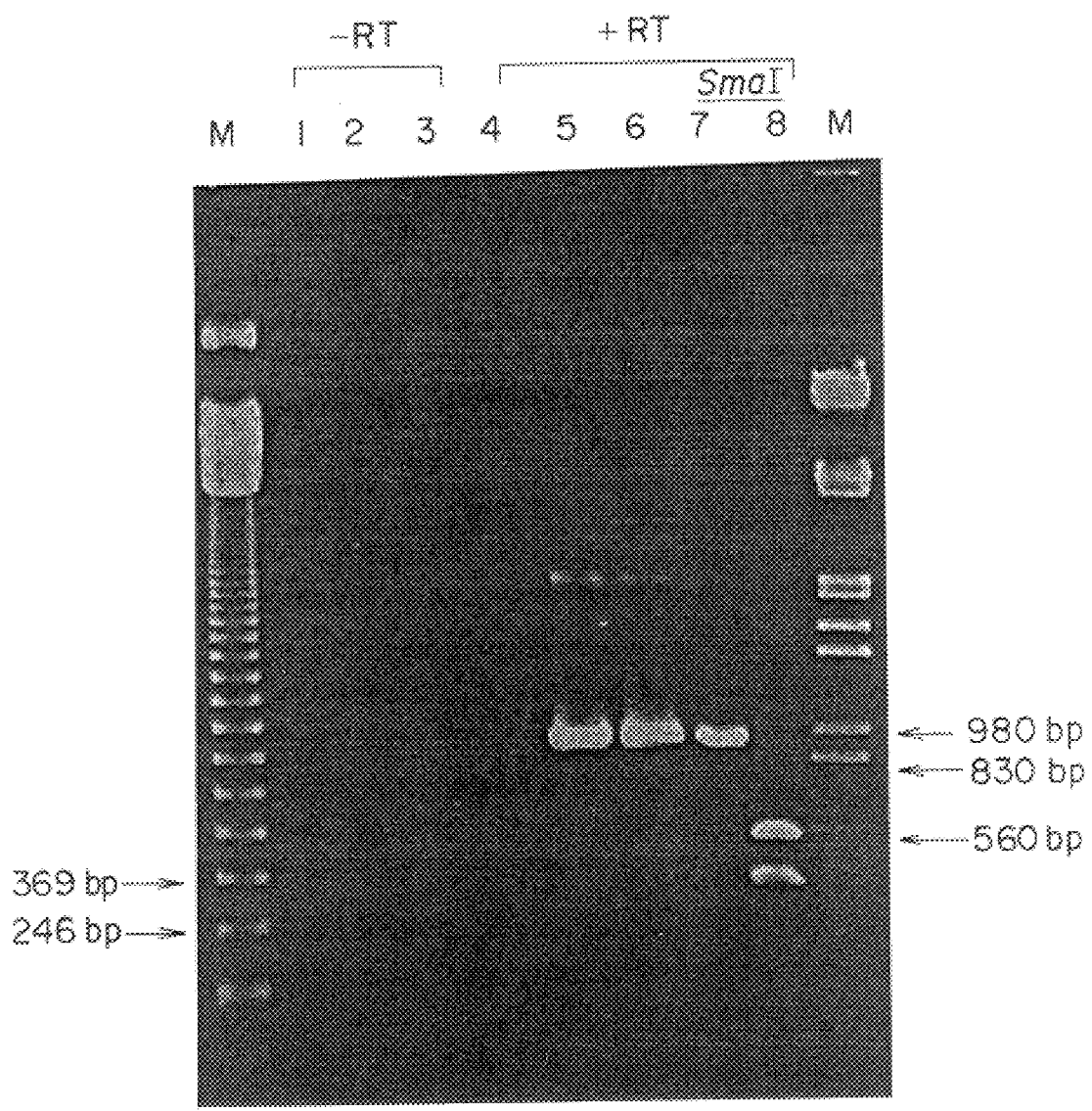
FIG. 5. Analysis of the RT-PCR products to identify the tagged sequence in segment B of recovered viruses. Genomic RNA isolated from recovered viruses were amplified by RT-PCR using segment B-specific primers B-BstR (binding to nucleotide positions 2285–2305; see table 1) and B-SacF (binding to positions 1351–1371; see table 1), and the products were analyzed on 1% agarose. A 954-bp fragment was obtained from recovered viruses (lanes 5 and 6), but not from the CHSE cells (lane 4) or the control(s) in which reverse transcriptase was omitted from the reaction (lanes 1–3). Gel-purified RT-PCR products were digested with SmaI, as indicated (lanes 7 and 8). Only the DNA derived from parental virus (recovered West Buxton, rWB) was digested to yield fragments of 403 and 551 bp (lane 8), whereas the DNA of the mutant virus remains undigested because of an elimination of this SmaI site by site-directed mutagenesis (lane 7). A 123-bp ladder (left lane M) and lambda DNA digested with HindlII/EcoRI (right lane M) were used as markers.

Identification of tagged sequence. To demonstrate the utility of the reverse genetics system, two recombinant IPNVs were generated. To introduce a tagged sequence in segment B, plasmid pUC19WBB-SmaI was constructed in which a unique internal SmaI site in the VP1 gene was eliminated by site-directed mutagenesis. Synthetic transcripts of this plasmid or pUC19WBB and pUC 19WBA were then used to transfect CHSE cells. To verify the presence or absence of mutation in recovered viruses, genomic RNA was isolated and analyzed by RT-PCR using a primer pair specific for segment B. FIG. 5 shows the analysis of RT-PCR products and SmaI-digested products of recovered viruses. A 954-bp fragment was obtained from both rWB and rWB-Sma viruses (lanes 5 and 6), but not from the CHSE cells (lane 4). Moreover, no PCR product was detected in mock-infected or IPNV-infected cells if the reverse transcriptase was omitted from the reaction before PCR (lanes 1–3). This indicates that the PCR product was derived from RNA and not from contaminating DNA. Digestion of PCR products with SmaI yielded expected fragments of 403 and 551 bp for rWB virus (lane 8), but remained undigested for rWB-Sma virus (lane 7). Furthermore, sequence analysis of this PCR product confirmed the expected nucleotide mutation (elimination of a SmaI site) in the VP1 gene. These results show that the tagged sequence is present in the genomic RNA of the recovered viruses.

Example 2
Construction of Full Length cDNA clones of IPNV strain SP

The cDNA clones containing the entire coding and noncoding regions of IPNV-RNA segments A and B were prepared using standard cloning procedures and methods, as described above for IPNV strain WB (K. Yao and V. N. Vakharia, J. Virol. 72:8913–8920, 1998). Based on the available sequence of the WB strain, including 5'- and 3'-terminal sequences, several primer pairs were synthesized and employed in RT-PCR amplifications.

To generate cDNA clones of segment A of SP strain, two primer pairs (A-A5'NC plus SpA-KpnR, SpA-KpnF plus SpA-PstR) were used for RT-PCR amplification. The sequences of these primers are:
1) A-A5'NC, 5'-TMTACGACTCACTATA GGAAAGAGAGTTTCMCG-3'(SEQ ID NO:2)
2) SpA-KpnR, 5'-GGCCATGGAGTGGTACCTTC-3'(SEQ ID NO:3)
3) SpA-KpnF, 5'-GMGGTACCACTCCATGGCC-3'(SEQ ID NO:4)
4) SpA-PstR, 5'-AMGCTTCTGCAGGGGG CCCCCTGGGGGGC-3'(SEQ ID NO:5)

Using genomic RNA as a template, desired overlapping cDNA fragments of segment A were synthesized and amplified according to the supplier's protocol (Perkin-Elmer). Amplified fragments were cloned into the EcoRI site of a pCR2.1 vector (Invitrogen Corp.) to obtain plasmids pCR-SpA5'#1 and SpA3'#6 (FIG. 1). The inserted DNA in all these plasmids was sequenced by the dideoxy chain termination method, using an Applied Biosystem automated DNA sequencer, and the sequence data was analyzed using PC/GENE (Intelligenetics) software. To construct a full-length cDNA clone of segment A, plasmids pCRSpA5'#1 and SpA3'#6 were double-digested with restriction enzyme pairs BamHI plus KpnI and KpnI plus HindIII release 1495 and 1602 bp fragments, respectively. These fragments were then cloned between the BamHI and KpnI sites of pUC19 vector to obtain plasmid pUC19SpA. This plasmid contains a full-length copy of segment A, which encodes all of the structural and nonstructural proteins (FIG. 1).

Similarly, to prepare cDNA clones of segment B, two primer pairs (B-B5'NC plus SpBIR and SpBIF plus B-Bgl3'NC) were used to generate overlapping cDNA fragments of segment B by RT-PCR amplification. The sequences of these primers are:
1) B-B5'NC, 5'-TMTACGACTCACTATA GGAAACAGTGGGTCAACG-3'(SEQ ID NO:6)
2) SpBIR, 5'-GTTGATCCCCGTCTTTGCTTCG-3'(SEQ ID NO:7)
3) SpBIF, 5'-CTTCCTCMCMCCATCTCATG-3'(SEQ ID NO:8)
4) B-Bgl3'NC, 5'-AGATCTGGGGTCCCTGGCGGMC-3' (SEQ ID NO:9)

Figure 2:
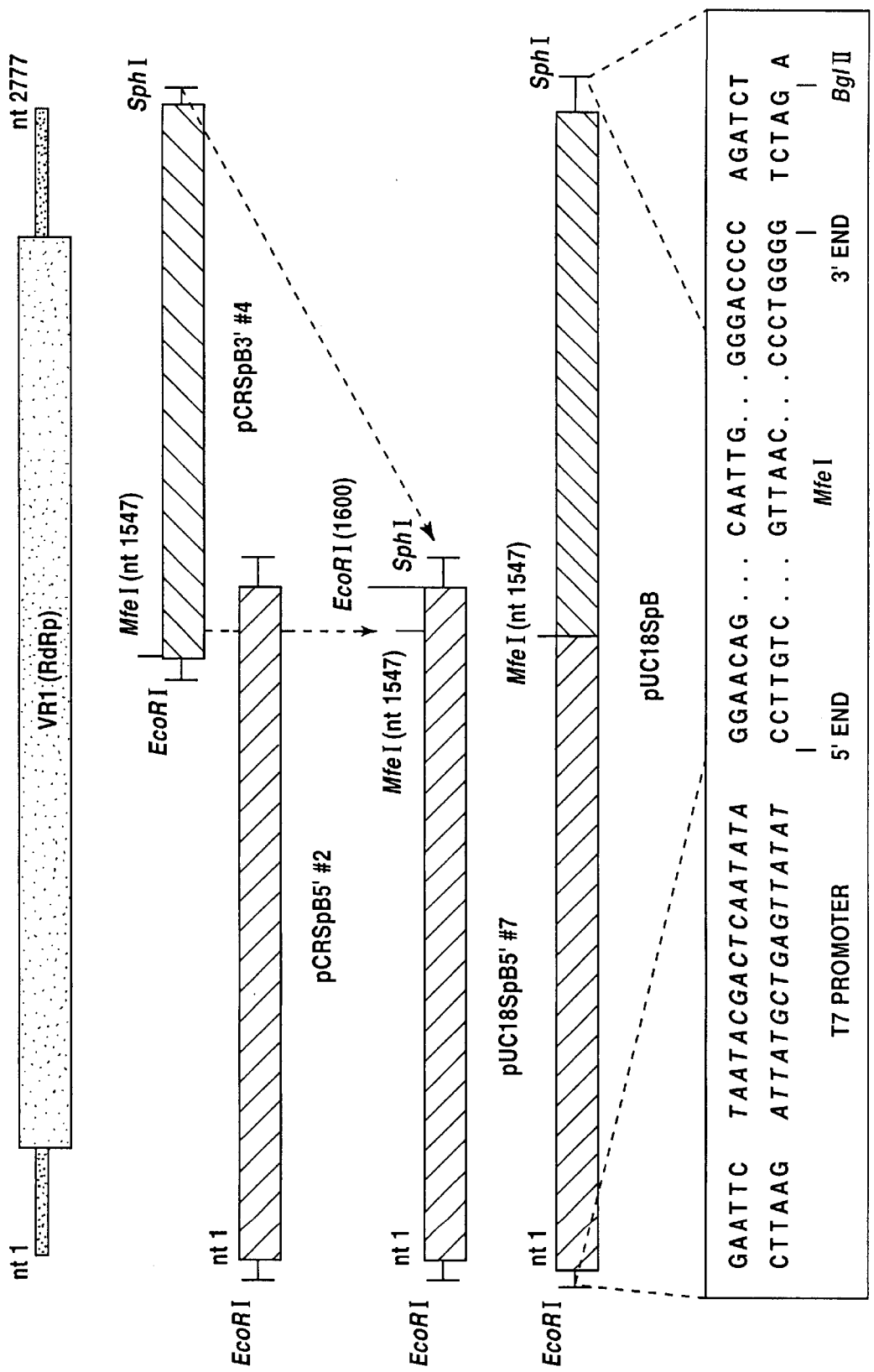
FIG. 2. Construction of the full-length cDNA clone of IPNV segment B for the synthesis of plus-sense RNA transcript with T7 RNA polymerase. The genome segment B of IPNV encodes the RNA-dependent RNA polymerase, VP1, which is shown at the top. Overlapping cDNA segments of IPNV were cloned into a pCR2.1 vector to obtain various pCR clones, as shown. Finally, a full-length plasmid pUC18SpB was obtained from these two clones, which contains a T7 RNA polymerase promoter sequence at its 5'-end. Restriction enzymes used for the construction of the above plasmids or linearization of the full-length clone are indicated (SEQ ID NO. 42,43).

Amplified fragments were cloned into pCR2.1 vectors to obtain plasmids pCRSpB5'#2 and pCRSpB3'#4, respectively (FIG. 2). Plasmid pCRSpB5'#2 was digested with EcoRI and subcloned into dephosphorylated EcoRI-cut pUC18 vector to obtain plasmid pUCSpB5'#7. To construct a full-length clone of segment B, DNA from plasmid pCR-SpB3'#4 was double-digested with MfeI plus SphI enzymes, and the resultant 1230-bp fragment was cloned into the MfeI-SphI digested pUC18SpB5'#7 vector. A representative clone of segment B was selected and designated pUC18SpB, which encodes VP1 protein (FIG. 2).

To introduce a mutation which would ablate the expression of 16-kDa nonstructural protein in segment A of SP strain, plasmid pUCSpANSdelta was constructed by oligonucleotide-directed mutagenesis using specific primer pairs and PCR amplification of the parent plasmid pUC19SpA. To construct pUCSpANSdelta, two primer pairs (SPNSdeltaF plus BstER and SPNSdeltaR plus pUCNdeF) were synthesized and used to amplify the DNA fragments. The sequences of these primers are:
1) SPNSdeltaF, 5'-CMTCTATATGCTAGCMGATGM-3' (SEQ ID NO.10)
2) SPNSdeltaR, 5'-GTTCATCTTGCTAGCATATAGATTG-3'(SEQ ID NO.11)
10 3) BstER, 5'-CTCCTTTGGTCACCAGCT-3'(SEQ ID NO.12)
4) PUCNdeF, 5'-CCATATGCGGTGTGAAATACCG-3' (SEQ ID NO.13)

Amplified DNA fragments were separated by agarose gel electrophoresis, gel purified, combined and subsequently amplified by PCR using the flanking primers (pUCNdeF and BstER) to generate an 800-bp fragment. This fragment was cloned into a pCR2.1 vector to obtain plasmid pCRSPNS-delta. This plasmid was digested with NdeI and BstEII, and the resulting fragment was cloned back into NdeI—BstEII-cleaved parent plasmid pUC19SpA to obtain plasmid pUC-SpANSdelta. As a result of this site-directed mutagenesis, the initiation codon for the 16-kDa protein was mutated to prevent the expression of this nonstructural protein.

The integrity of these full-length constructs was tested by in vitro transcription and translation coupled reticulocyte lysate system using T7 RNA polymerase (Promega Corp.). Preparation of RNA transcripts, transfection procedures, and recovery of IPNV was carried out essentially as described above for IPNV strain WB (K. Yao and V. N. Vakharia, J. Virol. 72:8913–8920, 1998).

Example 3
Generation of a Nonstructural Protein Deficient Mutant IPNV

Cells and viruses. See Example 1.

Construction of full-length cDNA clones. All manipulations of DNAs are performed according to standard protocols (Sambrook, J., et al., 1989, Molecular Cloning: A Laboratory Manual, 2nd ed. Cold Spring Harbor Laboratory, Cold Spring Harbor, N.Y.). Construction of a full-length cDNA clone of IPNV genome segment A of strain Sp is described above. It encodes all of the structural proteins (VP2, NS protease, and VP3), as well as the NS protein (FIG. 1). A mutant cDNA clone of segment A lacking the initiation codon of the NS gene is constructed by site directed mutagenesis as described in example 2. A mutant clone of segment A is obtained in which the ATG of the NS gene is mutated to ATT.

A cDNA clone of segment B of IPNV is constructed as discussed in example 2.

The DNA of the plasmids produced above was sequenced by dideoxy chain termination method (Sanger, F., et al., 1977, Proc. Natl. Acad. Sci. USA, 74: 5463–5467) using an Automated DNA Sequencer (Applied Biosystem), and the sequence data was analyzed using PC/Gene (Intelligenetics) software. The integrity of the full-length constructs is tested by in vitro transcription and translation coupled reticulocyte lysate system using T7 RNA polymerase (Promega Corp.).

Transcription, and transfection of synthetic RNAs. Transcription and transfection assays were performed as described in detail above. CHSE cells were transfected with combined transcripts of mutant segment A, and segment B, using Lipofectin reagent (GIBCO/BRL).

Growth curve of IPNV. To analyze the growth characteristics of IPNV, CHSE cells (in T-25 flasks) are infected with the parental strain or with transcript-derived unmodified or NS deficient virus stocks at an multiplicity of infection (MOI) of 0.1. Infected cell cultures are harvested at different time intervals and the titer of infectious virus present in the culture is determined by plaque assay on CHSE cells.

Assays for cell viability. For a cell viability assay, CHSE cells are infected with parental strain or with transcript-derived unmodified or NS deficient virus stocks at an multiplicity of infection (MOI) of 1. Cell viability was measured by trypan blue exclusion or by colorimetric MTT (tetrazolium) assay (Mosmann, T.,1983, J. Immuno. Methods 65:1170–1174).

Salmon inoculation and serology. Atlantic salmon fry can be used for the vaccine trials. The fry are divided into groups of 10–20 fish and each group is held in an aquarium throughout the course of the experiment.

The NS deficient virus is used for vaccination of the Atlantic salmon fry by immersion. The water level in the tanks is lowered and $2 \times 10^5$ pfu/ml of the NS deficient virus is added. Exposure to the vaccine is for 3 hours at this concentration; the water level is increased and then water flow is resumed.

Twenty days after the vaccination, the fry are challenged with the SP strain of IPNV. Virus is added to the tanks at a concentration $2 \times 10^5$ pfu/ml. Symptomatic fish are collected on a daily basis and examined to confirm the presence of the virus.

Characterization of recovered viruses in vivo. To detect and isolate the viruses from the salmon inoculated with the transfectant viruses, the pancreas from each sampled salmon is ground in PBS to make 10% pancreatic suspension. One-half ml pancreatic homogenate is mixed with 4.5 ml of M199 medium and passed through a 0.45 μm syringe filter. The filtrate is used to infect CHSE cells in a T-75 flask. The cells are examined daily (up to 5 days) for the presence or absence of IPNV-specific cytopathic effect. In addition, the titer of the virus present in these cultures is determined by plaque assays on CHSE cells.

Identification of recovered viruses by RT-PCR. Total nucleic acids of uninfected and IPNV-infected CHSE cells or pancreatic homogenates are isolated and analyzed by RT-PCR, respectively. RT-PCR reactions can be performed essentially as described earlier. The reaction products are separated by one percent agarose gel electrophoresis, and purified by using QlAquick gel extraction kit (QIAGEN Inc.). The PCR fragment, comprising the NS gene and the 5'-noncoding region of segment A, is cloned into a pCR2.1 vector, and sequenced as described above.

Fish inoculation and serology. The fish were inoculated as follows.

| Group | I | II | III | IV |
|---|---|---|---|---|
| Tank | 1 | 2 | 3 | 4 |
| Fish | 20 fry | 20 fry | 10 parr | 10 parr |
| Isolate | A: Sp-mutant | B: Sp-wildtype | A: Sp-mutant | B: Sp-wildtype |
| Challenge method | Immersion | Immersion | Injection | Injection |
| Challenge dose | $2 \times 10^5$ PFU/ml | $2 \times 10^5$ PFU/ml | $1.8 \times 10^5$ PFU | $2 \times 10^6$ PFU |

-continued

| Parameter | Requirements |
|---|---|
| Salinity | 0% |
| Temperature | 12° C. |
| Oxygen | 6–10 mg O2/liter $H_2O$ |
| Flow | Flow should be kept at a level to ensure sufficient $O_2$ |
| Size | Fry = 1g, Parr = 17 g |

Challenge. The fish were allowed to acclimatize, and normal behavior was observed prior to challenge. The fish were taken off feed for one day before challenge. Freshly prepared culture supernatants from CHSE-214 cells infected with the two challenge strains were used for challenge. The titers of the supernatants were determined by titration on CHSE-214 cells by standard procedure.

1. The two groups of fry (group I and II) were challenged by immersion by the following procedure. The water level in the tanks was reduced to 1 liter, and the water supply was turned off for 3 hours. 23 ml of the Sp mutant were added to group 1, giving a challenge dose of $2\times10^5$ PFU/ml. 18 ml of the Sp-wildtype were added to group II, giving a challenge dose of $2\times10^5$ PFU/ml.

Aeration was reinforced during the 3 hours bath. After 3 hours, water flow and volume in each tank were returned to normal.

2. The two groups of parr (group III and IV) were challenged by intraperitoneal injection of 0.2 ml (approx. $2\times10^6$ PFU) of the Sp mutant and a Sp wildtype respectively.

Sampling. 6, 8 and 10 days post challenge four fry from each of group I and II were sampled, opened and transferred immediately to tubes with 4% phosphate-buffered formaldehyde. At the same time pancreatic tissue was removed from 3 fish from each of group III and IV, and transferred to tubes containing 4% phosphate-buffered formaldehyde. Samples from untreated fish from the same stocks of fish used for vaccination, were sampled and used as negative controls. All samples were embedded in paraffin, cut in 5–6 micrometer thick slices, and placed on glue-coated slides. The specimens were stained with hematoxylin and eosin, and examined for degeneration and necrosis in exocrine pancreas.

At 8 days post infection the control fish infected with a virulent isolate of IPNV show a moderate inflammatory reaction, the exocrine tissue has almost disappeared with only a few exocrine cells remaining. The few remaining exocrine cells have indistinct cell borders (degenerate cells) with released zymogen granules. At 8 days post infection the fish infected with the IPNV mutant show no histopathological changes in exocrine tissue. The exocrine pancreas has a normal appearance with no histomorphological signs of degeneration.

TABLE I

Oligonucleotides used for the construction of full-length cDNA clones of IPNV genomic segments A and B

| Nucleotide sequence | Orientation | Designation | Nucleotide No. |
|---|---|---|---|
| *TAATACGACTCACTATA*GGAAAGAGAGTTTCAACG | + | A-A5'NC | 1–18 (SEQ ID NO. 14) |
| GTACCTCCTTGGTGCGATTG | − | A-ApaR | 711–731 (SEQ ID NO. 15) |
| GGTCAACAACCAACTAGTGACC | + | A-ApaF | 571–593 (SEQ ID NO. 16) |
| CTGAATCAGGTGTGATGC | − | A-SalR | 2222–2240 (SEQ ID NO. 17) |
| GTAGACATCAAAGCCAT | + | A-SalF | 2129–2146 (SEQ ID NO. 18) |
| GAAGATCTCCCGGGGGCCCCCTGGGGGGCC | − | A-A3'NC | 3078–3097 (SEQ ID NO. 19) |
| CCAACCGACATGGACAAGATCA | + | A-A3'F | 2753–2774 (SEQ ID NO. 20) |
| GTCCTGTGATGTTTCCAACCAC | − | A-A5'R | 361–382 (SEQ ID NO. 21) |
| *TAATACGACTCACTATA*GGAAACAGTGGGTCAACG | + | B-B5'NC | 1–18 (SEQ ID NO. 22) |
| GAAGGTAAGTTGCTTCAGMGCG | − | B-HindR | 477–500 (SEQ ID NO. 23) |
| GGACGATGGCAAGCTTAAGGACAC | + | B-HindF | 352–375 (SEQ ID NO. 24) |
| GTGTTGTCCTGCAGTATGTAGATG | − | B-PstR | 1267–1291 (SEQ ID NO. 25) |
| AGAGACAGTCTGGACAA | + | B-PstF | 1217–1233 (SEQ ID NO. 26) |
| AAGATCTGGGGTCCCTGGCGGAAC | − | B-BG13'NC | 2766–2783 (SEQ ID NO. 27) |
| GAAGATCTCCCGGGGTCCCTGGCGGAACCGGATGTTAT | − | B-Sma3'NC | 2756–2783 (SEQ ID NO. 28) |

TABLE I-continued

Oligonucleotides used for the construction of full-length cDNA clones of IPNV genomic segments A and B

| Nucleotide sequence | Orientation | Designation | Nucleotide No. |
|---|---|---|---|
| CAAGAGAGGCACTGGAGACCAT | + | B-B3'F | 2454–2475 (SEQ ID NO. 29) |
| GTAGAATGCAGTGGTTCCTTCTG | – | B-B5'R | 385–408 (SEQ ID NO. 30) |
| CGGAAACCCGGAGCCGAGATTG | + | B-SmaΔF | 1898–1919 (SEQ ID NO. 31) |
| CAATCTCGGCTCCGGGTTTCCG | – | B-SmaΔR | 1898–1919 (SEQ ID NO. 32) |
| CATGATGTACTACCTCCTGAC | + | B-SacF | 1351–1371 (SEQ ID NO. 33) |
| GATGCCTGGAACGACATGTCA | + | B-BstF | 2060–2080 (SEQ ID NO. 34) |
| GAGTTTGGTCCTTTGGTCTAG | – | B-BstR | 2285–2305 (SEQ ID NO. 35) |

Composition and location of the oligonucleotide primers used for cloning. T7 promoter sequences are marked with italic type, the virus specific sequences and underlined, and the restriction sites marked in boldface. Orientation of the virus-specific sequences of the primer is show for sense (+) and antisense (–). The positions where the primers blind (nucleotide number) are according to the published sequences of Jasper strain.

TABLE 2

Recovery of infectious pancreatic necrosis viruses following transfection of CHSE cells with cloned-derived plus-strand transcript of genomic segment A and B

| Transcripts derived from plasmids | Treatment | CPE on day |
|---|---|---|
| pUC19WBA pUC19WBB | None | 12 |
| pUC19WBA pUC19WBB-Sma | None | 10 |
| pUC19WBA pUC19WBB-Sma | DNAse treated | 10 |
| pUC19WBA pUC19WBB-Sma | RNase treated | — |
| pUC19WBA pUC19WBB-Sma | Uncapped | — |
| pUC19WBA | None | — |
| pUC19WBB | None | — |
| Lipofectin only | None | — |

```
ID IPNWBA   PRELIMINARY; DNA; 3097 BP.
DE WEST BUXTON, CLONE#4(SMAI SITE)
SQ SEQUENCE 3097 BP; 885 A; 891 C; 795 G; 526 T; 0 OTHER;
```

GGAAAGAGAG TTTCAACGTT AGTGGTAACC CACGAGCGGA GAGCTCTTAC GGAGGAGCTC    (SEQ ID NO. 36)

TCCATCGATG GCGAAAGCCC TTTCTAACAA ACAACCAACA ATTCTATTTA CATGAATCAT

GAACACAACA AAGGCAACCG CAACTTACTT GAGATCCATT ATGCTTCCCG AGAATGGACC

AGCAAGCATT CCGGACGACA TAACAGAGAG ACACATACTA AAACAAGAGA CCTCATCATA

CAACTTAGAG GTCTCCGACT CAGGAAGTGG GCTTCTTGTC TGCTTCCCTG GGGCTCCCGG

ATCCAGAGTC GGTGCCCACT ACAGGTGGAA TCTGAACCAG ACGGAACTGG AATTCGACCA

GTGGTTGGAA ACATCACAGG ACCTGAAGAA AGCATTCAAC TACGGGAGGT TGATCTCACG

GAAATACGAC ATCCAGAGCT CGACCCTTCC CGCTGGCCTC TATGCACTCA ACGGGACCCT

GAATGCAGCT ACCTTCGAAG GAAGTCTTTC TGAGGTGGAG AGCCTGACCT ATAACAGCTT

-continued

```
GATGTCCCTG ACAACAAACC CTCAGGACAA GGTCAACAAC CAACTAGTGA CCAAAGGAAT
AACCGTCCTG AACCTTCCAA CTGGGTTTGA CAAGCCATAC GTCCGCCTTG AGGACGAGAC
ACCGCAGGGC CCCCAGTCCA TGAACGGAGC CAGGATGAGG TGCACCGCTG CAATCGCACC
AAGGAGGTAC GAAATAGACC TCCCATCTGA GCGCCTACCA ACCGTGGCAG CAACTGGGAC
CCCAACAACA ATCTATGAAG GGAACGCCGA CATTGTGAAC TCAACCACAG TGACAGGAGA
CGTAACCTTC CAACTAGCAG CCGAACCCGT CAACGAGACG CGGTTCGACT TCATCCTACA
ATTCCTTGGG CTTGACAATG ATGTGCCCGT GGTCTCCGTG ACAAGCTCAA CCCTGGTCAC
GGCCGACAAC TACAGGGGTG CCTCCGCCAA GTTTACGCAG TCAATCCCAA CGGAACTAAT
AACTAAGCCC ATTACAAGGG TCAAGCTGGC TTACCAGCTC AACCAGCAGA CCGCAATCGG
AAACGCCGCA ACACTCGGGG CCAAAGGACC CCCGTCAGTC TCATTCTCAT CAGGGAATGG
CAATGTGCCG GGGGTTCTAA GACCCATAAC CTTGGTGGCA TACGAAAAGA TGACCCCCCA
GTCAATTCTG ACCGTGGCCG GCGTATCCAA CTATGAGCTG ATCCCCAACC CAGACCTCCT
GAAGAACATG GTCACCAAGT ATGGCAAATA TGACCCTGAG GGCCTCAACT ATGCCAAGAT
GATCCTGTCC CACAGGGAGG AGCTAGACAT TAGAACTGTC TGGAGGACCG AGGAGTACAA
GGAGAGGACA AGAGCCTTCA ATGAGATCAC TGACTTCACA AGTGACCTGC AACATCAAA
AGCATGGGGG TGGAGAGACC TGGTCAGAGG CATCAGAAAA GTGGCAGCAC CAGTGCTGTC
AACGCTCTTC CCAATGGCCG CCCCACTTAT AGGTGCGGCC GACCAGTTCA TCGGTGACCT
CACCAAGACC AACTCAGCCG GGGGCGCTA CCTGTCACAT GCAGCTGGAG GCCGCTACCG
TGATGTCATG GACACATGGG CTAGTGGCTC CGAGACAGGA AGCTACTCAA AGCACCTTAA
GACCCGGCTT GAGTCCAACA ACTATGAGGA AGTGGAGCTT CCCAAGCCAA CAAAAGGAGT
CATCTTTCCT GTGGTGCACA CCGTAGAAAG TGCACCAGGT GAGGCCTTCG GGTCGCTCGT
GGTTGTGATA CCAGGAGCAT ACCCGGAACT TCTTGACCCA AACCAACAGG TCCTATCCTA
CTTCAAGAAC GACACAGGCT GTGTCTGGGG GATAGGAGAA GACATTCCAT TTGAAGGAGA
TGACATGTGC TACACCGCAC TGCCCCTAAA GGAGATCAAA AGGAACGGCA ACATCGTAGT
GGAGAAAATA TTCGCTGGCC CTGCGATGGG ACCGTCGGCC CAACTTGCGC TGTCCCTACT
AGTCAACGAC ATAGACGAGG GGATTCCAAG GATGGTCTTC ACAGGGGAGA TTGCTGATGA
CGAGGAAACA GTCATCCCGA TCTGCGGAGT AGACATCAAA GCCATTGCCG CCCATGAACA
TGGGCTGCCA CTCATTGGCT GCCAACCAGG GGTCGACGAG ATGGTGGCAA ACACATCTCT
CGCATCACAC CTGATTCAGA GCGGCGCCCT ACCAGTGCAG AAAGCACAGG GGGCCTGCAG
GAAAATCAAG TACCTGGGCC AACTGATGAG AACAACTGCA TCAGGGATGG ACGAAGAACT
GCAGGGGCTG CTGCAGGCCA CCATGGCCAG AGCAAAGGAA GTCAAGGACG CCGAGGTGTT
CAAACTCCTG AAGCTGATGT CCTGGACACG GAAGAACGAC CTCACAGACC ACATGTACGA
GTGGTCAAAA GAGGACCCTG ATGCAATCAA GTTTGGCAGG CTCATCAGCA CCCCCCCAAA
ACACCAAGAG AAGCCAAAAG GACCTGACCA GCACACCGCC CAGGAGGCAA AGCAACCAG
AATATCACTG GACGCCGTCA AGCCGGAGC AGACTTTGCC TCACCCGAGT GGATTGCAGA
GAACAACTAC CGCGGTCCAG CTCCAGGTCA GTTCAAGTAC TACATGATAA CGGGCAGAGT
CCCAAACCCC GGAGTAGAGT ACGAGGACTA CGTGCGAAAA CCGATAACCC GACCAACCGA
CATGGACAAG ATCAGACGCC TAGCCAACAG TGTTTACGGA CTACCCCACC AAGAGCCCGC
ACCGGACGAC TTCTACCAAG CAGTCGTCGA GGTGTTTGCC GAGAATGGGG GGAGAGGACC
CGACCAAGAC CAAATGCAAG ACCTGAGGGA CTTGGCAAGG CAGATGAAAC GACGACCCAG
```

-continued

```
ACCAGCTGAT GCACGCAGGC AAACCAGGAC TCCACCGAGG GCGGCAACCT CCGGTGGTTC

ACGGTTTACC CCCTCCGGCG ACGACGGAGA AGTGTAACGG CTACTCTCTT TCCTGACTGA

TCCCCTGGCC TTAACCCCGG CCCCCCAGGG GGCCCCC
```

| Start | Stop | |
|---|---|---|
| 112 | 513 | = 16 kDa NS protein |
| 119 | 3037 | = 107 kDa polyprotein |

```
ID IPNWBB   PRELIMINARY; DNA; 2783 BP.
DE BSTEII PRIMER FOR 3'-END SEQUENCE, CLONE#8
SQ SEQUENCE 2783BP; 829 A; 813 C; 697 G; 444 T;0 OTHER;

GGAAACAGTG GGTCAACGTT GGTGGCACCC GACATACCAC GACTGTTTAT GTATGCACGC   (SEQ ID NO. 37)

AAGTGCCCCT TAACAAATCC CTATACACAC AACTCATGAT ATGTCGGACA TCTTCAACTC

ACCACAGAAC AAGGCTTCTA TCTTGAGCGC TCTAATGAGG AGCACAGCAG GAGATGTAGA

GGATGTGCTA ATACCAAAAC GCTTCAGGCC CGCCAAGGAC CCCCTTGACA ACCCTCAGGC

AGCAGCACAG TTCCTGAAGG ACAACAAGTA TCGGATACTT AGGCCGCGAG CCATTCCGAC

CATGGTCGAA CTAGAGACAG ATGCCGCTCT GCCCCGACTG CGACAAATGG TGGACGATGG

CAAGCTTAAG GACACGGTAA GCGTCCCAGA AGGAACCACT GCATTCTACC CCAAATACTA

TCCATTCCAC AAGCCAGACC ATGATGAGGT GGGGACGTTC GGGGCTCCGG ACATCACGCT

TCTGAAGCAA CTTACCTTCT TCCTGTTGGA GAACGACTTC CCCACAGGAC CAGAGACACT

CAGGCAGGTA CGTGAGGCCA TAGCTACACT CCAGTATGGA TCAGGCAGCT ACTCCGGACA

GCTAAACAGG CTCCTGGCCA TGAAGGGAGT TGCCACCGGC AGGAATCCAA ACAAGACTCC

AAAAACAGTA GGCTACACAA ACGAGCAGCT AGCAAAACTG CTGGAGCAGA CACTACCGAT

CAACACCCCA AAACATGAGG ACCCCGACCT CCGGTGGGCC CCCAGCTGGT TGATCAACTA

CACCGGAGAC CTGAGCACAG ACAAGTCATA CCTGCCACAC GTGACTATAA AGTCCTCAGC

CGGCCTACCC TACATAGGCA AAACCAAAGG AGACACGACT GCAGAGGCGC TCGTACTGGC

TGACTCCTTC ATACGTGACC TCGGAAAAGC AGCCACATCA GCCGATCCAG AAGCGGGAGT

GAAGAAAACC ATCACTGACT TCTGGTACCT GAGCTGTGGG CTGCTCTTCC CGAAGGGCGA

GAGATACACA CAGATTGACT GGGACAAGAA GACCAGGAAC ATCTGGAGTG CGCCCTACCC

AACACACCTA CTACTATCAA TGGTGTCATC CCCAGTAATG GACGAGTCAA AACTCAACAT

TACCAACACC CAGACACCAT CTCTGTATGG GTTCTCCCCA TTCCACGGAG GGATGGACAG

AATCATGACC ATCATCAGAG ACAGTCTGGA CAACAACGAG GACCTAGTGA TGATCTATGC

AGACAACATC TACATACTGC AGGACAACAC GTGGTACTCA ATAGACCTAG AAAAGGGCGA

GGCCAACTGC ACTCCACAAC ACATGCAGGC CATGATGTAC TACCTCCTGA CCAGGGGGTG

GACAAACGAG GATGGCTCTC CGCGGTACAA TCCGACATGG GCAACATTCG CCATGAATGT

GGCCCCGTCG ATGGTCGTGG ACTCCTCCTG TCTTCTGATG AACCTTCAGC TGAAGACCTA

CGGCCAGGGC AGTGGGAACG CCTTTACCTT CCTAAACAAC CACCTCATGT CAACGATCGT

CGTGGCCGAG TGGGTAAAAG CCGGGAAGCC AAACCCCATG ACAAAAGAGT TCATGGACCT

CGAGGAGAAG ACGGGGATCA ACTTTAAGAT AGAGCGCGAG CTAAAGAACT TGAGAGAAAC

CATCATCGAG GCCGTGGAGA CGGCCCCCCA GGATGGCTAC CTCGCCGATG GCTCCGATCT

ACCCCCGAAC AGACCAGGGA AAGCCGTCGA GCTAGACCTT CTTGGCTGGT CAGCCATCTA

CAGCCGCCAA ATGGAGATGT TCGTCCCAAT CCTCGAGAAC GAGCGACTAA TTGCCTCAGC
```

-continued

```
GGCCTACCCC AAGGGGCTTG AGAACAAGAC CCTGGCCCGG AAACCCGGGG CCGAGATTGC

GTACCAGATA GTGCGGTATG AAGCAATCAG GCTGGTGGGC GGCTGGAACA ATCCACTGCT

AGAAACCGCA GCCAAACACA TGTCCCTTGA CAAGAGAAAG AGACTGGAGG TGAAGGGGCT

GGACGTCACC GGGTTCCTAG ATGCCTGGAA CGACATGTCA GAATTCGGCG GAGACCTGGA

AGGCATAACG CTGTCCGAGC CCCTCACAAA CCAAACTCTG ATTGACATTA ACACACCCCT

GGAGAGCTTC GACCCCAAAG CCAGGCCACA AACACCACGG TCACCAAAGA AAACCCTGGA

CGAGGTGACG GCTGCCATTA CATCAGGGAC CTACAAGGAC CCCAAGAGCG CAGTGTGGCG

ACTGCTAGAC CAAAGGACCA AACTCCGGGT CAGCACACTG CGAGACCAAG CGTCAGCACT

GAAACCAGCC TCGTCCTCGG TCGACAACTG GGCCGAAGCC ACAGAGGAGC TAGCGGAGCA

ACAACAACTT CTCATGAAGG CCAACAACCT GCTAAAGAGC AGCTTGACGG AAACAAGAGA

GGCACTGGAG ACCATCCAGT CTGACAAAAT CATCACCGGG AAGTCCAACC CTGAAAAGAA

CCCAGGGACC GCAGCCAACC CAGTGGTTGG CTACGGGAAA TTCAGCGAGA AGATTCCTCT

GACTCCCACG CAGAAAAAGA ATGCCAAGCG GAGGGAGAAG CAGAGAAGAA ACCAGTAAGA

AGACCAAACC GGGAAGAATC CGAAATGACC CAGCTGGACT CATATGCAAG CTCCGCGCCG

TAAGGCAAGC TGAACCAAAG TAGTGACCCG ACAATGTGCC ACCAACATGA CCCCAGATAA

CATCCGGTTC CGCCAGGGAC CCC

Start                Stop 101                  2638 = 94 kDa (VP1) protein

ID SPA   PRELIMINARY; DNA; 3097 BP.
SQ SEQUENCE 3097 BP; 890 A; 932 C; 797 G; 478 T; 0 OTHER;

GGAAAGAGAG TTTCAACGTT AGTGGCAACC CACGAGCGGA GAGCTCTTAC GGAGGAGCTC   (SEQ ID NO. 38)

TCCGTCGATG GCGAAAGCCC TTTCTAACAA ACAAACAAAC AATCTATATC AATGCAAGAT

GAACACAAAC AAGGCAACCG CAACTTACTT GAAATCCATT ATGCTTCCAG AGACTGGACC

AGCAAGCATC CCGGACGACA TAACGGAGAG ACACATCTTA AAACAAGAGA CCTCGTCATA

CAACTTAGAG GTCTCCGAAT CAGGAAGTGG CATTCTTGTT TGTTTCCCTG GGCACCAGG

CTCACGGATC GGTGCACACT ACAGATGGAA TGCGAACCAG ACGGGCTGG AGTTCGACCA

GTGGCTGGAG ACGTCGCAGG ACCTGAAGAA AGCCTTCAAC TACGGGAGGT TGATCTCAAG

GAAATACGAC ATCCAAAGCT CCACACTACC GGCCGGTCTC TATGCTCTGA ACGGGACGCT

CAACGCTGCC ACCTTCGAGG GCAGTCTGTC TGAGGTGGAG AGCCTGACCT ACAACAGCCT

GATGTCCCTA ACAACGAACC CCAGGACAA AGTCAACAAC CAGCTGGTGA CCAAAGGAGT

CACAGTCCTG AATCTACCAA CAGGGTTCGA CAAGCCATAC GTCCGCCTAG AGGACGAGAC

ACCCCAGGGT CTCCAGTCAA TGAACGGGGC CAAGATGAGG TGCACAGCTG CAATTGCACC

GCGGAGGTAC GAGATCGACC TCCCATCCCA ACGCCTACCC CCCGTTCCTG CGACAGGGGC

CCTCACCACT CTCTACGAGG GAAACGCCGA CATCGTCAAC TCCACGACAG TGACGGGAGA

CATAAACTTC AGTCTGGCAG AACAACCCGC AGTCGAGACC AAGTTCGACT TCCAGCTGGA

CTTCATGGGC CTTGACAACG ACGTCCCAGT CGTCACAGTG GTCAGCTCCG TGCTGGCCAC

AAATGACAAC TACAGAGGAG TCTCAGCCAA GATGACCCAG TCCATCCCGA CCGAGAACAT

CACAAAGCCG ATCACCAGGG TCAAGCTGTC ATACAAGATC AACCAGCAGA CAGCAATCGG

CAACGTCGCC ACCCTGGGCA CAATGGGTCC AGCATCCGTC TCCTTCTCAT CAGGGAACGG
```

-continued

```
AAATGTCCCC GGCGTGCTCA GACCAATCAC ACTGGTGGCC TATGAGAAGA TGACACCGCT
GTCCATCCTG ACCGTAGCTG GAGTGTCCAA CTACGAGCTG ATCCCAAACC CAGAACTCCT
CAAGAACATG GTGACACGCT ATGGCAAGTA CGACCCCGAA GGTCTCAACT ATGCCAAGAT
GATCCTGTCC CACAGGGAAG AGCTGGACAT CAGGACAGTG TGGAGGACAG AGGAGTACAA
GGAGAGGACC AGAGTCTTCA ACGAAATCAC GGACTTCTCC AGTGACCTGC CCACGTCAAA
GGCATGGGGC TGGAGAGACA TAGTCAGAGG AATTCGGAAA GTCGCAGCTC CTGTACTGTC
CACGCTGTTT CCAATGGCAG CACCACTCAT AGGAATGGCA GACCAATTCA TTGGAGATCT
CACCAAGACC AACGCAGCAG GCGGAAGGTA CCACTCCATG GCCGCAGGAG GGCGCCACAA
AGACGTGCTC GAGTCCTGGG CAAGCGGAGG GCCCGACGGA AAATTCTCCC GAGCCCTCAA
GAACAGGCTG GAGTCCGCCA ACTACGAGGA AGTCGAGCTT CCACCCCCCT CAAAAGGAGT
CATCGTCCCT GTGGTGCACA CAGTCAAGAG TGCACCAGGC GAGGCATTCG GGTCCCTGGC
AATCATAATT CCAGGGGAGT ACCCCGAGCT TCTAGATGCC AACCAGCAGG TCCTATCCCA
CTTCGCAAAC GACACCGGGA GCGTGTGGGC CATAGGAGAG GACATACCCT TCGAGGGAGA
CAACATGTGC TACACTGCAC TCCCACTCAA GGAGATCAAA GAAACGGGA ACATAGTAGT
CGAGAAGATC TTTGCTGGAC CAATCATGGG TCCCTCTGCT CAACTAGGAC TGTCCCTACT
TGTGAACGAC ATCGAGGACG GAGTTCCAAG GATGGTATTC ACCGGCGAAA TCGCCGATGA
CGAGGAGACA ATCATACCAA TCTGCGGTGT AGACATCAAA GCCATCGCAG CCCATGAACA
AGGGCTGCCA CTCATCGGCA ACCAACCAGG AGTGGACGAG GAGGTGCGAA ACACATCCCT
GGCCGCACAC CTGATCCAGA CCGGAACCCT GCCCGTACAA CGCGCAAAGG CTCCAACAA
GAGGATCAAG TACCTGGGAG AGCTGATGGC ATCAAATGCA TCCGGGATGG ACGAGGAACT
GCAACGCCTC CTGAACGCCA CAATGGCACG GGCCAAAGAA GTCCAGGACG CCGAGATCTA
CAAACTTCTT AAGCTCATGG CATGGACCAG AAAGAACGAC CTCACCGACC ACATGTACGA
GTGGTCAAAA GAGGACCCCG ATGCACTAAA GTTCGGAAAG CTCATCAGCA CGCCACCAAA
GCACCCTGAG AAGCCCAAAG GACCAGACCA ACACCACGCC CAAGAGGCGA GAGCCACCCG
CATATCACTG GACGCCGTGA GAGCCGGGGC GGACTTCGCC ACACCGGAAT GGGTCGCGCT
GAACAACTAC CGCGGCCCAT CTCCCGGGCA GTTCAAGTAC TACCTGATCA CTGGACGAGA
ACCAGAACCA GGCGACGAGT ACGAGGACTA CATAAAACAA CCCATTGTGA AACCAACCGA
CATGTACAAA ATCAGACGTC TAGCCAACAG TGTGTACGGC CTCCCACACC AGGAACCAGC
ACCAGAGGAG TTCTACGATG CAGTTGCAGC TGTATTCGCA CAGAACGGAG GCAGAGGTCC
CGACCAGGAC CAAATGCAAG ACCTCAGGGA GCTCGCAAGA CAGATGAAAC GACGACCCCG
GAACGCCGAT GCACCACGGA GAACCAGAGC GCCAGCGGAA CCGGCACCGC CCGGACGCTC
AAGGTTCACC CCCAGCGGAG ACAACGCTGA GGTGTAACGA CTACTCTCTT TCCTGACTGA
TCCCCTGGCC AAAACCCCGG CCCCCCAGGG GGCCCCC
```

```
          Start               Stop 112                 513  = 15 kDa NS protein 68 or 119           3037 = 107-108 kDa polyprotein 1444                2100 = 25 kDa putative protein
```

ID SPB  PRELIMINARY; DNA; 2777 BP.
SQ SEQUENCE 2777 BP; 842 A; 803 C; 675 G; 457 T; 0 OTHER;

```
GGAAACAGTG GGTCAACGTT GGTGGCACCC GACATACCAC GACTGTTTAT GTATGCACGC   (SEQ ID NO. 39)

GAGTGCCCCT TTTAAAACCT CTACAATATA CAACTTATGA TATGTCGGAC ATCTTCAATT

CACCTCAGAA CAAGGCTTCT ATCTTGAATG CACTCATGAA GAGCACGCAG GGAGACGTGG

AGGATGTTCT AATACCCAAG CGGTTCAGAC CCGCAAAGGA TCCGTTAGAT AGCCCCCAGG

CTGCAGCCGC GTTCCTGAAA GAACACAAGT ATCGGATACT TAGGCCGCGA GCCATACCCA

CCATGGTTGA ATAGAGACG GATGCCGCTC TGCCTCGACT AGCGGCCATG GTGGATGATG

GCAAGCTTAA GGAAATGGTC AATGTTCCCG AAGGAACAAC CGCGTTCTAC CCAAAATACT

ACCCATTCCA CAAACCCGAC CATGACGACG TGGGAACGTT TGGGGCTCCA GACATGACAC

TACTCAAACA ACTGACGTTC TTCCTGCTGG AGAATGACTT TCCAACTGGT CCAGAAACCC

TAAGACAAGT CAGAGAAGCA ATCGCAACCC TGCAATACGG GTCCGGCAGC TACTCAGGAC

AACTCAACAG GCTACTGGCA ATGAAGGGCG TCGCCACGGG GAGGAATCCC AACAAGACTC

CACTGGCCGT TGGCTATACC AACGAGCAGA TGGCAAGACT GATGGAGCAA ACCTTGCCTA

TCAACCCTCC AAAGAATGAG GACCCAGACC TCCGATGGGC CCCAAGCTGG TTGATACAGT

ACACCGGAGA CGCATCAACT GACAAGTCAT ATCTCCCTCG TGTGACAGTC AAGTCATCTG

CCGGCCTACC CTACATAGGC AAAACCAAAG GAGACACCAC GGCCGAAGCC CTGGTGCTGG

CAGACTCCTT CATAAGGGAC CTCGGAAAAG CCGCAACATC AGCCGACCCA GAGGCGGACG

TCAAGAAAGT ACTGTCCGAC TTCTGGTACC TCAGCTGCGG TCTGCTCTTC CCAAAAGGGG

AGAGATACAC ACAGAAAGAC TGGGACCTGA AGACCAGGAA CATCTGGAGT GCCCCCTATC

CAACGCACCT ACTACTATCA ATGGTGTCGT CACCGGTGAT GGATGAGTCA AAACTCAACA

TCACCAACAC TCAGACCCCT TCTCTGTACG GGTTCTCACC ATTCCACGGT GGGATCAACA

GAATCATGAC CATCATCAGA GAGCATCTAG ATCAAGAGCA GGACCTAGTC ATGATATATG

CCGACAACAT ATACATACTA CAGGACAACA CCTGGTACTC CATCGATCTA GAAAAGGGAG

AAGCAAACTG CACACCACAA CACATGCAGG CAATGATGTA CTACCTGCTC ACACGCGGAT

GGACAAACGA GGACGGCTCA CCACGGTACA ACCCGACGTG GGCAACATTT GCCATGAACG

TTGGGCCCTC AATGGTAGTG GACTCAACCT GCCTGCTGAT GAATCTGCAG CTGAAGACCT

ACGGGCAAGG CAGTGGGAAT GCCTTCACCT TCCTCAACAA CCATCTCATG TCCACAATTG

TGGTCGCGGA GTGGCACAAA GCAGGAAGGC CAAATCCCAT GTCCAAAGAA TTCATGGACC

TCGAAGCAAA GACGGGGATC AACTTCAAAA TCGAGCGCGA GCTGAAAGAC CTAAGGTCGA

TCATCATGGA GGCGGTAGAC ACCGCCCCAC TCGACGGCTA TCTAGCCGAC GGGTCCGACC

TGCCACCCAG GGTGCCAGGG AAGGCGGTGG AGCTCGACCT TCTAGGATGG TCCGCAGTGT

ACAGCCGACA ACTCGAGATG TTCGTCCCCG TCCTTGAAAA CGAAAGACTA ATTGCATCAG

TCGCCTACCC AAAAGGGCTA GAGAACAAAT CCCTAGCTCG AAAACCCGGG GCCGAGATCG

CATACCAAAT AGTAAGGTAT GAAGCGATTC GGCTCATCGG AGGCTGGAAC AATCCACTCA

TCGAAACAGC AGCAAAACAC ATGTCCCTGG ACAAAAGGAA GAGACTGGAG GTAAAAGGCA

TCGACGTCAC CGGATTCCTA GACGACTGGA ACACCATGTC GGAGTTCGGA GGCGATCTAG

AGGGCATCTC ACTAACAGCT CCCCTCACAA ACCAGACTCT CCTAGACATC AACACACCAG

AGACCGAGTT CGACGTCAAA GACAGACCCC CCACGCCGCG TTCCCCAGGC AAAACCCTCG

CCGAGGTAAC CGCAGCGATA ACATCAGGGA CCTACAAAGA CCCCAAAAGT GCAGTGTGGA

GGCTCCTCGA CCAGAGGACC AAACTACGCG TGAGCACCCT ACGCGATCAG GCGCACGCGC

TAAAACCCGC AGCGTCAACA TCCGACAACT GGGGGGACGC CACAGAAGAA CTCGCCGAAC
```

-continued

```
AACAACAGCT GCTGATGAAG GCGAACAACC TGCTAAAGAG CAGCCTCACG GAAGCGAGGG

AAGCCCTCGA AACCGTGCAG TCAGACAAAA TAATCTCAGG CAAAACCTCT CCAGAGAAGA

ATCCCGGGAC CGCCGCAAAC CCCGTGGTTG GCTATGGAGA ATTTAGCGAG AAAATTCCTC

TCACTCCCAC GCAAAAGAAG AACGCCAAGC GTCGGGAGAA GCAGAGAAGA AACTAAGAAC

GAAGACCAGG GAGCATCCGA AATGAAATGG ATGGACTCAC AAGAGCTCCG CGCCAGAAGG

CAATCCAGAC CAAAGTAGTG ACCTGAGACA GTGCCACCAA CATGACCCCA GATAACATCG

GTTCCGCCAG GGACCCC
```

```
          Start              Stop 102                2636 = 94 kDa protein
```

What is claimed is:

1. A method for producing a live, infectious pancreatic necrosis virus, comprising the following steps:
preparing at least one cDNA of infectious pancreatic necrosis virus genome segments A and B,
initiating replication of a ds RNA in a host cell using RNA derived from said cDNA,
incubating said host cell in a culture medium, and
isolating live, infectious pancreatic necrosis virus from said culture medium.

2. The method according to claim 1, wherein said cDNA contains epitopic determinants from at least two different strains of infectious pancreatic necrosis virus.

3. A method for preparing nonpathogenic, infectious pancreatic necrosis virus, comprising the following steps:
preparing a cDNA containing infectious pancreatic necrosis virus genome segments A and B, wherein the cDNA of segment A is modified to prevent the expression of NS protein,
transcribing said cDNA to produce synthetic RNA transcripts,
transfecting host cells with said synthetic RNA transcripts,
incubating said host cells in a culture medium, and
isolating live, nonpathogenic infectious pancreatic necrosis virus from said culture medium.

4. The method according to claim 3, wherein said host cells are selected from the group consisting of chinook salmon embryo cells, Rainbow trout gonad cells, Bluegill fish cells, Brown Bullhead cells, and Fathead Minnow cells.

5. The method according to claim 3, wherein said cDNA is derive from more than one strain of infectious pancreatic necrosis virus.

6. The method according to claim 3, wherein the cDNA for segment A is modified by mutating the initiation codon of the NS gene to a stop codon.

7. A method for producing a live, nonpathogenic, infectious pancreatic necrosis virus vaccine, comprising the steps of
preparing a full-length cDNA containing infectious pancreatic necrosis virus genome segments A and B, wherein segment A has been modified to prevent expression of NS protein,
transcribing said cDNA to produce synthetic RNA transcripts,
transfecting host cells with said RNA transcripts,
incubating said host cells in a culture medium,
isolating live infectious, nonpathogenic pancreatic necrosis virus from said culture medium, and
combining said live, nonpathogenic infectious pancreatic necrosis virus with a pharmaceutically acceptable carrier to produce a live, nonpathogenic, infectious pancreatic necrosis virus vaccine.

8. A method for generating a nonpathogenic, chimeric virus, comprising the following steps:
preparing a cDNA containing infectious pancreatic necrosis virus genome segments A and B, wherein the cDNA of segment A is modified to prevent the expression of NS protein and said cDNA of segment A encodes epitopic determinants from at least two different infectious pancreatic necrosis virus strains,
transcribing said cDNA to produce synthetic RNA transcripts,
transfecting host cells with said synthetic RNA transcripts,
incubating said host cells in a culture medium, and
isolating live, nonpathogenic, chimeric, infectious pancreatic necrosis virus from said culture medium.

9. A cDNA containing at least a portion of the infectious pancreatic necrosis virus genome selected from the group consisting of segment A, and segments A and B, wherein said cDNA includes the 5' and 3' terminal of said segments and wherein segment A is modified to prevent expression of NS protein.

10. The cDNA according to claim 9, wherein said cDNA is derived from more than one strain of infectious pancreatic necrosis virus.

11. A recombinant vector comprising the cDNA according to claim 9.

12. A host cell transformed with the recombinant vector according to claim 11.

13. A synthetic RNA transcribed from the cDNA according to claim 9.

14. A host cell transformed with a synthetic RNA according to claim 13.

15. A live, nonpathogenic infectious pancreatic necrosis virus, wherein said infectious pancreatic necrosis virus strain is selected from the group consisting of West Buxton, Jasper and SP, and wherein said virus is made by a process comprising the steps of
preparing a cDNA containing infectious pancreatic necrosis virus genome segments A and B, wherein segment A is modified to prevent the expression of NS protein,
transcribing said cDNA to produce a synthetic RNA transcript,
transfecting a host cell with said synthetic RNA transcript,
incubating said host cell in a culture medium, and
isolating live, nonpathogenic, infectious pancreatic necrosis virus from said culture medium.

16. A vaccine comprising an infectious, nonpathogenic pancreatic necrosis virus according to claim 15, wherein segment A of said virus is modified in at least two regions to prevent the expression of NS protein.

17. A nonpathogenic, chimeric, aquatic Birnavirus, wherein said virus is deficient in the expression of the NS protein and contains epitopic determinants from at least two different Birnavirus strains, and wherein said aquatic Birnavirus is infectious pancreatic necrosis virus.

18. The virus according to claim 17, wherein said infectious pancreatic necrosis virus strains are selected from the group consisting of West Buxton, Jasper and SP.

19. A vaccine comprising the nonpathogenic, chimeric, aquatic Birnavirus according to claim 17, in combination with a pharmaceutically acceptable carrier.

20. The vaccine according to claim 19, further comprising antigens from aquatic viruses other than Birnavirus, bacterial antigens or antigens from aquatic viruses other than Birnaviruses in combination with bacterial antigens.

21. The vaccine according to claim 20, wherein said antigens from aquatic viruses other than Birnaviruses are selected from the group consisting of infectious hematopoietic necrosis virus (IHNV), viral hemorrhagic septicemia virus (VHSV), ISAV (Infectious salmon anemia virus), PDV (Pancreas disease virus), Irido virus, and Nodavirus.

22. The vaccine according to claim 20, wherein said bacterial antigens are antigens from gram negative bacteria.

23. The vaccine according to claim 20 wherein said bacterial antigens are antigens from gram positive bacteria.

24. The vaccine according to claim 20 wherein said bacterial antigens are from bacteria selected from the group consisting of Aeromonas salmonicda, Vibrio anguillarum, Vibrio salmonicida, Vibrio viscosus, Yersinia ruckri, Piscirickettsia salmonis, Renibacterium salmoninarum, Pasturella piscicida, Flavobacterium columnare, Flavobacterium psychrophilum, and Lactococcus garvieae.

* * * * *

SEQUENCE LISTING

<160> NUMBER OF SEQ ID NOS: 51

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: synthetic

<400> SEQUENCE: 1
gcggccgccc ttttttttttt tttttt                                    26

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: synthetic

<400> SEQUENCE: 2
taatacgact cactatagga aagagagttt caacg                            35

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 3
ggccatggag tggtaccttc                                             20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 4
gaaggtacca ctccatggcc                                             20

<210> SEQ ID NO 5
<211> LENGTH: 30
<212> TYPE: DNA
<213> ORGANISM: Artificial Sequence
```

```
<220> FEATURE:
<223> OTHER INFORMATION: Description of Artificial Sequence: synthetic

<400> SEQUENCE: 5
aaagcttctg cagggggccc cctgggggc                                    30

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: synthetic

<400> SEQUENCE: 6
taatacgact cactatagga aacagtgggt caacg                             35

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 7
gttgatcccc gtctttgctt cg                                           22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 8
cttcctcaac aaccatctca tg                                           22

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: synthetic

<400> SEQUENCE: 9
agatctgggg tccctggcgg aac                                          23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: synthetic

<400> SEQUENCE: 10
caatctatat gctagcaaga tgaa                                         24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: synthetic

<400> SEQUENCE: 11
gttcatcttg ctagcatata gattg                                        25
```

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: synthetic

<400> SEQUENCE: 12
ctcctttggt caccagct                                                18

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 13
ccatatgcgg tgtgaaatac cg                                           22

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: synthetic

<400> SEQUENCE: 14
taatacgact cactatagga aagagagttt caacg                             35

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: synthetic

<400> SEQUENCE: 15
gtacctcctt ggtgcgattg                                              20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 16
ggtcaacaac caactagtga cc                                           22

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: synthetic

<400> SEQUENCE: 17
ctgaatcagg tgtgatgc                                                18

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: synthetic

```
<400> SEQUENCE: 18
gtagacatca aagccat                                                  17

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: synthetic

<400> SEQUENCE: 19
gaagatctcc cgggggcccc ctgggggggcc                                   30

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 20
ccaaccgaca tggacaagat ca                                            22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 21
gtcctgtgat gtttccaacc ac                                            22

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: synthetic

<400> SEQUENCE: 22
taatacgact cactatagga aacagtgggt caacg                              35

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: synthetic

<400> SEQUENCE: 23
gaaggtaagt tgcttcagaa gcg                                           23

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: synthetic

<400> SEQUENCE: 24
ggacgatggc aagcttaagg acac                                          24

<210> SEQ ID NO 25
```

```
<211> LENGTH: 24
<212> TYPE: DNA
<213> ORGANISM: Artificial Sequence
<220> FEATURE:
<223> OTHER INFORMATION: Description of Artificial Sequence: synthetic

<400> SEQUENCE: 25
gtgttgtcct gcagtatgta gatg                                               24

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: synthetic

<400> SEQUENCE: 26
agagacagtc tggacaa                                                       17

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: synthetic

<400> SEQUENCE: 27
aagatctggg gtccctggcg gaac                                               24

<210> SEQ ID NO 28
<211> LENGTH: 38
<212> TYPE: DNA
<213> ORGANISM: Artificial Sequence
<220> FEATURE:
<223> OTHER INFORMATION: Description of Artificial Sequence: synthetic

<400> SEQUENCE: 28
gaagatctcc cggggtccct ggcggaaccg gatgttat                                38

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 29
caagagaggc actggagacc at                                                 22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: synthetic

<400> SEQUENCE: 30
gtagaatgca gtggttcctt ctg                                                23

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 31
```
cggaaacccg gagccgagat tg                                        22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: synthetic

<400> SEQUENCE: 32
caatctcggc tccgggtttc cg                                        22

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: synthetic

<400> SEQUENCE: 33
catgatgtac tacctcctga c                                         21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: synthetic

<400> SEQUENCE: 34
gatgcctgga acgacatgtc a                                         21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: synthetic

<400> SEQUENCE: 35
gagtttggtc ctttggtcta g                                         21

<210> SEQ ID NO 36
<211> LENGTH: 3097
<212> TYPE: DNA
<213> ORGANISM: Infectious pancreatic necrosis virus

<400> SEQUENCE: 36
ggaaagagag tttcaacgtt agtggtaacc cacgagcgga gagctcttac ggaggagctc      60
tccatcgatg gcgaaagccc tttctaacaa acaaccaaca attctattta catgaatcat     120
gaacacaaca aaggcaaccg caacttactt gagatccatt atgcttcccg agaatggacc     180
agcaagcatt ccggacgaca taacagagag acacatacta aaacaagaga cctcatcata     240
caacttagag gtctccgact caggaagtgg gcttcttgtc tgcttccctg gggctcccgg     300
atccagagtc ggtgcccact acaggtggaa tctgaaccag acggaactgg aattcgacca     360
gtggttggaa acatcacagg acctgaagaa agcattcaac tacgggaggt tgatctcacg     420
gaaatacgac atccagagct cgaccccttcc cgctggcctc tatgcactca acgggaccct     480
gaatgcagct accttcgaag gaagtctttc tgaggtggag agcctgacct ataacagctt     540
gatgtccctg acaacaaacc ctcaggacaa ggtcaacaac caactagtga ccaaaggaat     600

-continued

```
aaccgtcctg aaccttccaa ctgggtttga caagccatac gtccgccttg aggacgagac    660
accgcagggc ccccagtcca tgaacggagc caggatgagg tgcaccgctg caatcgcacc    720
aaggaggtac gaaatagacc tcccatctga gcgcctacca accgtggcag caactgggac    780
cccaacaaca atctatgaag ggaacgccga cattgtgaac tcaaccacag tgacaggaga    840
cgtaaccttc caactagcag ccgaacccgt caacagacg cggttcgact tcatcctaca     900
attccttggg cttgacaatg atgtgcccgt ggtctccgtg acaagctcaa ccctggtcac    960
ggccgacaac tacaggggtg cctccgccaa gtttacgcag tcaatcccaa cggaactaat   1020
aactaagccc attacaaggg tcaagctggc ttaccagctc aaccagcaga ccgcaatcgg   1080
aaacgccgca acactcgggg ccaaaggacc cccgtcagtc tcattctcat cagggaatgg   1140
caatgtgccg ggggttctaa gacccataac cttggtggca tacgaaaaga tgaccccca    1200 gtcaattctg accgtggccg gcgtatccaa ctatgagctg atccccaacc cagacctcct   1260
gaagaacatg gtcaccaagt atggcaaata tgaccctgag ggcctcaact atgccaagat   1320
gatcctgtcc cacagggagg agctagacat tagaactgtc tggaggaccg aggagtacaa   1380
ggagaggaca agagccttca atgagatcac tgacttcaca agtgacctgc aacatcaaa   1440 agcatggggg tggagagacc tggtcagagg catcagaaaa gtggcagcac cagtgctgtc   1500
aacgctcttc ccaatggccg ccccacttat aggtgcggcc gaccagttca tcggtgacct   1560
caccaagacc aactcagccg gggggcgcta cctgtcacat gcagctggag gccgctaccg   1620
tgatgtcatg gacacatggg ctagtggctc cgagacagga agctactcaa agcaccttaa   1680
gacccggctt gagtccaaca actatgagga agtggagctt cccaagccaa caaaaggagt   1740
catctttcct gtggtgcaca ccgtagaaag tgcaccaggt gaggccttcg ggtcgctcgt   1800
ggttgtgata ccaggagcat acccggaact tcttgaccca aaccaacagg tcctatccta   1860
cttcaagaac gacacaggct gtgtctgggg gataggagaa gacattccat ttgaaggaga   1920
tgacatgtgc tacaccgcac tgcccctaaa ggagatcaaa aggaacggca acatcgtagt   1980
ggagaaaata ttcgctggcc ctgcgatggg accgtcggcc caacttgcgc tgtccctact   2040
agtcaacgac atagacgagg ggattccaag gatggtcttc acaggggaga ttgctgatga   2100
cgaggaaaca gtcatcccga tctgcggagt agacatcaaa gccattgccg cccatgaaca   2160
tgggctgcca ctcattggct gccaaccagg ggtcgacgag atggtggcaa acacatctct   2220
cgcatcacac ctgattcaga gcggcgccct accagtgcag aaagcacagg gggcctgcag   2280
gaaaatcaag tacctgggcc aactgatgag aacaactgca tcagggatgg acgaagaact   2340
gcaggggctg ctgcaggcca ccatggccag agcaaaggaa gtcaaggacg ccgaggtgtt   2400
caaactcctg aagctgatgt cctggacacg gaagaacgac ctcacagacc acatgtacga   2460
gtggtcaaaa gaggaccctg atgcaatcaa gtttggcagg ctcatcagca ccccccaaa    2520 acaccaagag aagccaaaag gacctgacca gcacaccgcc caggaggcaa aagcaaccag   2580
aatatcactg gacgccgtca agccggagc agactttgcc tcacccgagt ggattgcaga    2640
gaacaactac cgcggtccag ctccaggtca gttcaagtac tacatgataa cgggcagagt   2700
cccaaacccc ggagtagagt acgaggacta cgtgcgaaaa ccgataaccc gaccaaccga   2760
catggacaag atcagacgcc tagccaacag tgtttacgga ctaccccacc aagagcccgc   2820
accggacgac ttctaccaag cagtcgtcga ggtgtttgcc gagaatgggg ggagaggacc   2880
cgaccaagac caaatgcaag acctgaggga cttggcaagg cagatgaaac gacgacccag   2940
accagctgat gcacgcaggc aaaccaggac tccaccgagg gcggcaacct ccggtggttc   3000
```
acggtttacc ccctccggcg acgacggaga agtgtaacgg ctactctctt tcctgactga    3060 tccctggcc ttaaccccgg ccccccaggg ggccccc                               3097

<210> SEQ ID NO 37
<211> LENGTH: 2783
<212> TYPE: DNA
<213> ORGANISM: Infectious pancreatic necrosis virus

<400> SEQUENCE: 37
ggaaacagtg ggtcaacgtt ggtggcaccc gacataccac gactgtttat gtatgcacgc      60
aagtgcccct taacaaatcc ctatacacac aactcatgat atgtcggaca tcttcaactc     120
accacagaac aaggcttcta tcttgagcgc tctaatgagg agcacagcag gagatgtaga     180
ggatgtgcta ataccaaaac gcttcaggcc cgccaaggac ccccttgaca accctcaggc     240
agcagcacag ttcctgaagg acaacaagta tcggatactt aggccgcgag ccattccgac     300
catggtcgaa ctagagacag atgccgctct gccccgactg cgacaaatgg tggacgatgg     360
caagcttaag gacacggtaa gcgtcccaga aggaaccact gcattctacc ccaaatacta     420
tccattccac aagccagacc atgatgaggt ggggacgttc ggggctccgg acatcacgct     480
tctgaagcaa cttaccttct tcctgttgga gaacgacttc cccacaggac agagacact      540 caggcaggta cgtgaggcca tagctacact ccagtatgga tcaggcagct actccggaca     600
gctaaacagg ctcctggcca tgaagggagt gccaccggc aggaatccaa acaagactcc     660
aaaaacagta ggctacacaa cgagcagct agcaaaactg ctggagcaga cactaccgat     720
caacacccca aaacatgagg acccccgacct ccggtgggcc cccagctggt tgatcaacta     780
caccggagac ctgagcacag acaagtcata cctgccacac gtgactataa agtcctcagc     840
cggcctaccc tacataggca aaaccaaagg agacacgact gcagaggcgc tcgtactggc     900
tgactccttc atacgtgacc tcggaaaagc agccacatca gccgatccag aagcgggagt     960
gaagaaaacc atcactgact tctggtacct gagctgtggg ctgctcttcc cgaagggcga    1020
gagatacaca cagattgact gggacaagaa gaccaggaac atctggagtg cgccctaccc    1080
aacacaccta ctactatcaa tggtgtcatc cccagtaatg gacgagtcaa aactcaacat    1140
taccaacacc cagacaccat ctctgtatgg gttctcccca ttccacggag ggatggacag    1200
aatcatgacc atcatcagag acagtctgga caacaacgag gacctagtga tgatctatgc    1260
agacaacatc tacatactgc aggacaacac gtggtactca atagacctag aaaagggcga    1320
ggccaactgc actccacaac acatgcaggc catgatgtac tacctcctga ccaggggtg    1380 gacaaacgag gatggctctc cgcggtacaa tccgacatgg gcaacattcg ccatgaatgt    1440
ggccccgtcg atggtcgtgg actcctcctg tcttctgatg aaccttcagc tgaagaccta    1500
cggccagggc agtgggaacg cctttacctt cctaaacaac cacctcatgt caacgatcgt    1560
cgtggccgag tgggtaaaag ccgggaagcc aaaccccatg acaaaagagt tcatggacct    1620
cgaggagaag acgggatca actttaagat agagcgcgag ctaaagaact tgagagaaac    1680
catcatcgag gccgtggaga cggcccccca ggatggctac ctcgccgatg ctccgatct    1740 accccgaac agaccaggga agccgtcga gctagacctt cttggctggt cagccatcta    1800
cagccgccaa atggagatgt tcgtcccaat cctcgagaac gagcgactaa ttgcctcagc    1860
ggcctacccc aaggggcttg agaacaagac cctggcccgg aaaccggggg ccgagattgc    1920
gtaccagata gtgcggtatg aagcaatcag gctggtgggc ggctggaaca atccactgct    1980

-continued

```
agaaaccgca gccaaacaca tgtcccttga caagagaaag agactggagg tgaagggct    2040 ggacgtcacc gggttcctag atgcctggaa cgacatgtca gaattcggcg gagacctgga    2100
aggcataacg ctgtccgagc ccctcacaaa ccaaactctg attgacatta acacaccct     2160 ggagagcttc gaccccaaag ccaggccaca acaccacgg tcaccaaaga aaaccctgga     2220
cgaggtgacg gctgccatta catcagggac ctacaaggac cccaagagcg cagtgtggcg    2280
actgctagac caaaggacca aactccgggt cagcacactg cgagaccaag cgtcagcact    2340
gaaaccagcc tcgtcctcgg tcgacaactg ggccgaagcc acagaggagc tagcggagca    2400
acaacaactt ctcatgaagg ccaacaacct gctaaagagc agcttgacgg aaacaagaga    2460
ggcactggag accatccagt ctgacaaaat catcaccggg aagtccaacc ctgaaaagaa    2520
cccagggacc gcagccaacc cagtggttgg ctacgggaa ttcagcgaga agattcctct     2580
gactcccacg cagaaaaaga atgccaagcg agggagaag cagagaagaa accagtaaga     2640
agaccaaacc gggaagaatc cgaaatgacc cagctggact catatgcaag ctccgcgccg    2700
taaggcaagc tgaaccaaag tagtgacccg acaatgtgcc accaacatga ccccagataa    2760
catccggttc cgccagggac ccc                                            2783
```

<210> SEQ ID NO 38
<211> LENGTH: 3097
<212> TYPE: DNA
<213> ORGANISM: Infectious pancreatic necrosis virus

<400> SEQUENCE: 38

```
ggaaagagag tttcaacgtt agtggcaacc cacgagcgga gagctcttac ggaggagctc    60
tccgtcgatg gcgaaagccc tttctaacaa acaaacaaac aatctatatc aatgcaagat    120
gaacacaaac aaggcaaccg caacttactt gaaatccatt atgcttccag agactggacc    180
agcaagcatc ccggacgaca taacggagag acacatctta aaacaagaga cctcgtcata    240
caacttagag gtctccgaat caggaagtgg cattcttgtt tgtttccctg ggcaccagg     300 ctcacgatcg gtgcacact acagatggaa tgcgaaccag acggggctgg agttcgacca     360
gtggctggag acgtcgcagg acctgaagaa agccttcaac tacgggaggt tgatctcaag    420
gaaatacgac atccaaagct ccacactacc ggccggtctc tatgctctga acgggacgct    480
caacgctgcc accttcgagg gcagtctgtc tgaggtggag agcctgacct acaacagcct    540
gatgtcccta acaacgaacc cccaggacaa agtcaacaac cagctggtga ccaaaggagt    600
cacagtcctg aatctaccaa cagggttcga caagccatac gtccgcctag aggacgagac    660
accccagggt ctccagtcaa tgaacggggc caagatgagg tgcacagctg caattgcacc    720
gcggaggtac gagatcgacc tcccatccca acgcctaccc ccgttcctg cgacagggc     780 cctcaccact ctctacgagg gaaacgccga catcgtcaac tccacgacag tgacgggaga    840
cataaacttc agtctggcag aacaacccgc agtcgagacc aagttcgact ccagctggga    900
cttcatgggc cttgacaacg acgtcccagt cgtcacagtg gtcagctccg tgctggccac    960
aaatgacaac tacagaggag tctcagccaa gatgacccag tccatcccga ccgagaacat    1020
cacaaagccg atcaccaggg tcaagctgtc atacaagatc aaccagcaga cagcaatcgg    1080
caacgtcgcc accctgggca caatgggtcc agcatccgtc tccttctcat caggaacgg    1140 aaatgtcccc ggcgtgctca gaccaatcac actggtggcc tatgagaaga tgacaccgct    1200
gtccatcctg accgtagctg gagtgtccaa ctacgagctg atcccaaacc cagaactcct    1260
caagaacatg gtgacacgct atggcaagta cgaccccgaa ggtctcaact atgccaagat    1320
```

```
gatcctgtcc cacagggaag agctggacat caggacagtg tggaggacag aggagtacaa    1380
ggagaggacc agagtcttca acgaaatcac ggacttctcc agtgacctgc ccacgtcaaa    1440
ggcatggggc tggagagaca tagtcagagg aattcggaaa gtcgcagctc ctgtactgtc    1500
cacgctgttt ccaatggcag caccactcat aggaatggca gaccaattca ttggagatct    1560
caccaagacc aacgcagcag gcggaaggta ccactccatg gccgcaggag ggcgccacaa    1620
agacgtgctc gagtcctggg caagcggagg gcccgacgga aaattctccc gagccctcaa    1680
gaacaggctg gagtccgcca actacgagga agtcgagctt ccacccccct caaaaggagt    1740
catcgtccct gtggtgcaca cagtcaagag tgcaccaggc gaggcattcg ggtccctggc    1800
aatcataatt ccaggggagt accccgagct tctagatgcc aaccagcagg tcctatccca    1860
cttcgcaaac gacaccggga gcgtgtgggg cataggagag acataccct tcgagggaga    1920
caacatgtgc tacactgcac tcccactcaa ggagatcaaa agaaacggga acatagtagt    1980
cgagaagatc tttgctggac caatcatggg tccctctgct caactaggac tgtccctact    2040
tgtgaacgac atcgaggacg gagttccaag gatggtattc accggcgaaa tcgccgatga    2100
cgaggagaca atcataccaa tctgcggtgt agacatcaaa gccatcgcag cccatgaaca    2160
agggctgcca ctcatcggca accaaccagg agtggacgag gaggtgcgaa acacatccct    2220
ggccgcacac ctgatccaga ccggaaccct gcccgtacaa cgcgcaaagg gctccaacaa    2280
gaggatcaag tacctgggag agctgatggc atcaaatgca tccgggatgg acgaggaact    2340
gcaacgcctc ctgaacgcca aatggcacg ggccaaagaa gtccaggacg ccgagatcta    2400
caaacttctt aagctcatgg catggaccag aaagaacgac ctcaccgacc acatgtacga    2460
gtggtcaaaa gaggaccccg atgcactaaa gttcggaaag ctcatcagca cgccaccaaa    2520
gcaccctgag aagcccaaag gaccagacca acaccacgcc caagaggcga gagccacccg    2580
catatcactg gacgccgtga gagccggggc ggacttcgcc acaccggaat gggtcgcgct    2640
gaacaactac cgcggcccat ctcccgggca gttcaagtac tacctgatca ctggacgaga    2700
accagaacca ggcgacgagt acgaggacta cataaaacaa cccattgtga aaccaaccga    2760
catgtacaaa atcagacgtc tagccaacag tgtgtacggc ctcccacacc aggaaccagc    2820
accagaggag ttctacgatg cagttgcagc tgtattcgca cagaacggag gcagaggtcc    2880
cgaccaggac caaatgcaag acctcaggga gctcgcaaga cagatgaaac gacgaccccg    2940
gaacgccgat gcaccacgga gaaccagagc gccagcggaa ccggcaccgc ccggacgctc    3000
aaggttcacc cccagcggag acaacgctga ggtgtaacga ctactctctt tcctgactga    3060
tccctggcc aaaaccccgg cccccaggg ggcccc                               3097
```

<210> SEQ ID NO 39
<211> LENGTH: 2777
<212> TYPE: DNA
<213> ORGANISM: Infectious pancreatic necrosis virus

<400> SEQUENCE: 39

```
ggaaacagtg ggtcaacgtt ggtggcaccc gacataccac gactgtttat gtatgcacgc      60
gagtgcccct tttaaaacct ctacaatata caacttatga tatgtcggac atcttcaatt     120
cacctcagaa caaggcttct atcttgaatg cactcatgaa gagcacgcag ggagacgtgg     180
aggatgttct aatacccaag cggttcagac ccgcaaagga tccgttagat agcccccagg     240
ctgcagccgc gttcctgaaa gaacacaagt atcggatact taggccgcga gccatacccca    300
```

-continued

| | |
|---|---|
| ccatggttga aatagagacg gatgccgctc tgcctcgact agcggccatg gtggatgatg | 360 |
| gcaagcttaa ggaaatggtc aatgttcccg aaggaacaac cgcgttctac ccaaaatact | 420 |
| acccattcca caaacccgac catgacgacg tgggaacgtt tggggctcca gacatgacac | 480 |
| tactcaaaca actgacgttc ttcctgctgg agaatgactt tccaactggt ccagaaaccc | 540 |
| taagacaagt cagagaagca atcgcaaccc tgcaatacgg gtccggcagc tactcaggac | 600 |
| aactcaacag gctactggca atgaagggcg tcgccacggg gaggaatccc aacaagactc | 660 |
| cactggccgt tggctatacc aacgagcaga tggcaagact gatggagcaa accttgccta | 720 |
| tcaaccctcc aaagaatgag gacccagacc tccgatgggc cccaagctgg ttgatacagt | 780 |
| acaccggaga cgcatcaact gacaagtcat atctccctcg tgtgacagtc aagtcatctg | 840 |
| ccggcctacc ctacataggc aaaaccaaag gagacaccac ggccgaagcc ctggtgctgg | 900 |
| cagactcctt cataagggac ctcggaaaag ccgcaacatc agccgaccca gaggcggacg | 960 |
| tcaagaaagt actgtccgac ttctggtacc tcagctgcgg tctgctcttc ccaaaagggg | 1020 |
| agagatacac acagaaagac tgggacctga agaccaggaa catctggagt gcccctatc | 1080 |
| caacgcacct actactatca atggtgtcgt caccggtgat ggatgagtca aaactcaaca | 1140 |
| tcaccaacac tcagacccct tctctgtacg ggttctcacc attccacggt gggatcaaca | 1200 |
| gaatcatgac catcatcaga gagcatctag atcaagagca ggacctagtc atgatatatg | 1260 |
| ccgacaacat atacactga caggacaaca cctggtactc catcgatcta gaaaagggag | 1320 |
| aagcaaactg cacaccacaa cacatgcagg caatgatgta ctacctgctc acacgcggat | 1380 |
| ggacaaacga ggacgggctca ccacggtaca acccgacgtg ggcaacattt gccatgaacg | 1440 |
| ttgggccctc aatggtagtg gactcaacct gcctgctgat gaatctgcag ctgaagacct | 1500 |
| acgggcaagg cagtgggaat gccttcacct tcctcaacaa ccatctcatg tccacaattg | 1560 |
| tggtcgcgga gtgcacaaa gcaggaaggc caaatcccat gtccaaagaa ttcatggacc | 1620 |
| tcgaagcaaa gacggggatc aacttcaaaa tcgagcgcga gctgaaagac ctaaggtcga | 1680 |
| tcatcatgga ggcggtagac accgccccac tcgacggcta tctagccgac gggtccgacc | 1740 |
| tgccacccag ggtgccaggg aaggcggtgg agctcgacct tctaggatgg tccgcagtgt | 1800 |
| acagccgaca actcgagatg ttcgtccccg tccttgaaaa cgaaagacta attgcatcag | 1860 |
| tcgcctaccc aaaagggcta gagaacaaat ccctagctcg aaaacccggg gccgagatcg | 1920 |
| cataccaaat agtaaggtat gaagcgattc ggctcatcgg aggctggaac aatccactca | 1980 |
| tcgaaacagc agcaaaacac atgtccctgg acaaaaggaa gagactggag gtaaaaggca | 2040 |
| tcgacgtcac cggattccta gacgactgga caccatgtc ggagttcgga ggcgatctag | 2100 |
| agggcatctc actaacagct cccctcacaa accagactct cctagacatc aacacaccag | 2160 |
| agaccgagtt cgacgtcaaa gacagacccc ccacgccgcg ttccccaggc aaaaccctcg | 2220 |
| ccgaggtaac cgcagcgata acatcaggga cctacaaaga ccccaaaagt gcagtgtgga | 2280 |
| ggctcctcga ccagaggacc aaactacgcg tgagcaccct acgcgatcag cgcacgcgc | 2340 |
| taaaacccgc agcgtcaaca tccgacaact gggggacgc cacagaagaa ctcgccgaac | 2400 |
| aacaacagct gctgatgaag gcgaacaacc tgctaaagag cagcctcacg gaagcgaggg | 2460 |
| aagccctcga aaccgtgcag tcagacaaaa taatctcagg caaaacctct ccagagaaga | 2520 |
| atcccgggac cgccgcaaac cccgtggttg gctatggaga atttagcgag aaaattcctc | 2580 |
| tcactcccac gcaaaagaag aacgccagc gtcgggagaa gcagagaaga aactaagaac | 2640 |
| gaagaccagg gagcatccga aatgaaatgg atggactcac aagagctccg cgccagaagg | 2700 |

```
caatccagac caaagtagtg acctgagaca gtgccaccaa catgacccca gataacatcg    2760
gttccgccag ggacccc                                                    2777
```

<210> SEQ ID NO 40
<211> LENGTH: 51
<212> TYPE: DNA
<213> ORGANISM: Artificial Sequence
<220> FEATURE:
<223> OTHER INFORMATION: Description of Artificial Sequence: synthetic

<400> SEQUENCE: 40

```
ggatcctaat acgactcaat ataggaaaga ggggcccccc tgcagaagct t              51
```

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: synthetic

<400> SEQUENCE: 41

```
cctaggatta tgctgagtta tatcctttct cccggggggg acgtctctag a              51
```

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: synthetic

<400> SEQUENCE: 42

```
gaattctaat acgactcaat ataggaacag caattgggga ccccagatct                50
```

<210> SEQ ID NO 43
<211> LENGTH: 50
<212> TYPE: DNA
<213> ORGANISM: Artificial Sequence
<220> FEATURE:
<223> OTHER INFORMATION: Description of Artificial Sequence: synthetic

<400> SEQUENCE: 43

```
cttaagatta tgctgagtta tatccttgtc gttaacccct ggggtctaga                50
```

<210> SEQ ID NO 44
<211> LENGTH: 122
<212> TYPE: DNA
<213> ORGANISM: Infectious pancreatic necrosis virus

<400> SEQUENCE: 44
ggaaagagag tttcaacgtt agtggtaacc cacgagcgga gagctcttac ggaggagctc 60
tccgtcgatg gcgaaagccc tttctaacaa acaaccaaca attcttatct acatgaatca 120
tg 122

<210> SEQ ID NO 45
<211> LENGTH: 62
<212> TYPE: DNA
<213> ORGANISM: Infectious pancreatic necrosis virus

<400> SEQUENCE: 45
taacagctac tctctttcct gactgatccc ctggccgtaa ccccggcccc ccagggggcc 60
cc 62

```
<210> SEQ ID NO 46
<211> LENGTH: 103
<212> TYPE: DNA
<213> ORGANISM: Infectious pancreatic necrosis virus

<400> SEQUENCE: 46
ggaaacagtg ggtcaacgtt ggtggcaccc gacataccac gactgtttac gtatgcacgc      60
aagtgccctt taacaaaacc ctatacacac aactcatgat atg                        103

<210> SEQ ID NO 47
<211> LENGTH: 149
<212> TYPE: DNA
<213> ORGANISM: Infectious pancreatic necrosis virus

<400> SEQUENCE: 47
taagaagacc caaaccggga agaatccgaa atgaatcagc tggactcata tgaaagctcc      60
gcgccgcacg gcaagctgga caaaagtagt gacccgacaa cgtgccacca acatgacccc     120
tgaaaacatc cggttccgcc agggacccc                                        149

<210> SEQ ID NO 48
<211> LENGTH: 54
<212> TYPE: DNA
<213> ORGANISM: Artificial Sequence
<220> FEATURE:
<223> OTHER INFORMATION: Description of Artificial Sequence: synthetic

<400> SEQUENCE: 48
ggtacctaat acgactcaat ataggaagag ggaccccccg ggagatctct taag            54

<210> SEQ ID NO 49
<211> LENGTH: 54
<212> TYPE: DNA
<213> ORGANISM: Artificial Sequence
<220> FEATURE:
<223> OTHER INFORMATION: Description of Artificial Sequence: synthetic

<400> SEQUENCE: 49
ccatggatta tgctgagtta tatccttctc ccctgggggc cctctagaga attc            54

<210> SEQ ID NO 50
<211> LENGTH: 51
<212> TYPE: DNA
<213> ORGANISM: Artificial Sequence
<220> FEATURE:
<223> OTHER INFORMATION: Description of Artificial Sequence: synthetic

<400> SEQUENCE: 50
gaattctaat acgactcaat ataggaaaca ggggacccca gatctggatc c               51

<210> SEQ ID NO 51
<211> LENGTH: 51
<212> TYPE: DNA
<213> ORGANISM: Artificial Sequence
<220> FEATURE:
<223> OTHER INFORMATION: Description of Artificial Sequence: synthetic

<400> SEQUENCE: 51
cttaagatta tgctgagtga tatcctttgt cccctggggt ctagacctag g               51
```